United States Patent
Chung et al.

(10) Patent No.: US 8,071,764 B2
(45) Date of Patent: Dec. 6, 2011

(54) COMPOUNDS OF REVERSE TURN MIMETICS AND THE USE THEREOF (2)

(75) Inventors: Jae Uk Chung, Cheongju-si (KR);
Kyung-Yun Jung, Seongnam-si (KR);
Sang-Hwi Lee, Suwon-si (KR);
Myoung-Joo Kang, Hwaseong-si (KR)

(73) Assignee: Choongwae Pharma Corporation, Seoul (KR)

( * ) Notice: Subject to any disclaimer, the term of this patent is extended or adjusted under 35 U.S.C. 154(b) by 0 days.

(21) Appl. No.: 12/682,881

(22) PCT Filed: Oct. 15, 2008

(86) PCT No.: PCT/KR2008/006071
§ 371 (c)(1),
(2), (4) Date: Apr. 13, 2010

(87) PCT Pub. No.: WO2009/051398
PCT Pub. Date: Apr. 23, 2009

(65) Prior Publication Data
US 2010/0228027 A1    Sep. 9, 2010

(51) Int. Cl.
*C07D 487/04* (2006.01)
*A61K 31/53* (2006.01)
*A61P 35/00* (2006.01)

(52) U.S. Cl. .................... 544/184; 514/243
(58) Field of Classification Search .............. 544/184; 514/243
See application file for complete search history.

(56) References Cited

U.S. PATENT DOCUMENTS

| | | | |
|---|---|---|---|
| 5,440,013 A | 8/1995 | Kahn | |
| 5,929,237 A | 7/1999 | Kahn | |
| 6,013,458 A | 1/2000 | Kahn et al. | |
| 7,232,822 B2 * | 6/2007 | Moon et al. | 514/243 |
| 7,566,711 B2 * | 7/2009 | Moon et al. | 514/243 |
| 7,576,084 B2 * | 8/2009 | Moon et al. | 514/243 |
| 7,671,054 B1 * | 3/2010 | Moon et al. | 514/243 |

FOREIGN PATENT DOCUMENTS

| | | |
|---|---|---|
| WO | WO-94/03494 | 2/1994 |
| WO | WO-01/00210 A1 | 1/2001 |
| WO | WO-01/16135 A2 | 3/2001 |
| WO | WO 03/031448 A1 | 4/2003 |
| WO | WO 2005/116032 A2 | 12/2005 |

OTHER PUBLICATIONS

Tumelty et al, "Immobilised, Activated Peptides as Reagents for Cyclic and Derivatised Peptide Libraries," *J. Chem. Soc., Chem. Commun.*, pp. 1067-1070, 1994.
Eichler et al., "Cyclic Peptide Template Combinatorial Libraries: Synthesis and Identification of Chymotrypsin Inhibitors," *Peptide Research*, 7:300-306, 1994.
Obrecht et al., "Novel Peptide Mimetic Building Blocks and Strategies for Efficient Lead Finding," *Advances in Medicinal Chemistry*, Vo. 4, pp. 1-68, 1999.
Pelengaris et al., "The many faces of c-MYC," *Archives of Biochemistry and Biophysics*, vol. 416, pp. 129-136, 2003.
Hoffman et al., "The proto-oncogene c-*myc* in hematopoietic development and leukemogenesis," *Oncogene*, vol. 21, pp. 3414-3421, 2002.
Luo et al., "c-Myc rapidly induces acute myeloid leukemia in mice without evidence of lymphoma-associated antiapoptotic mutations," *Blood*, vol. 106, No. 7, pp. 2452-2461, Oct. 1, 2005.
Nakamura et al., "Trimethadione Metabolism, A Useful Indicator for Assessing Hepatic Drug-Oxidizing Capacity," *Biochemical Pharmacology*, vol. 47, No. 2, pp. 247-251, 1994.
Rendic et al., "Human Cytochrome P450 Enzymes: A Status Report Summarizing Their Reactions, Substrates, Inducers, and Inhibitors," *Drug Metabolism Reviews*, vol. 29 (1&2), 413-580 (1997).
Dresser et al., "Pharmacokinetic-Pharmacodynamic Consequences and Clinical Relevance of Cytochrome P450 3A4 Inhibition," *Clin Pharmacokinet*, vol. 38 pp. 41-57, Jan. 2000.
Cheng et al., "Effects of renal function on recainam pharmacokinetics and pharmacodynamics," *Clinical Pharmacology & Therapeutics*, vol. 567, No. 5, pp. 492-498, May 1995.
Fleisher et al., "Improved oral drug delivery: solubility limitations overcome by the use of prodrugs," *Advanced Drug Delivery Reviews*, pp. 115-130, 1996.
Davis et al., "ZD6126: A Novel Vascular-targeting Agent That Causes Selective Destruction of Tumor Vasculature," *Cancer Research*, vol. 62, pp. 7247-7253, Dec. 15, 2002.
Golik et al., "Synthesis and Antitumor Evaluation of Paclitaxel Phosphonooxymethyl Ethers: A Novel Class of Water Soluble Paclitaxel Pro-Drugs," *Bioorganic & Medicinal Chemistry Letters*, vol. 6, No. 15, pp. 1837-1842, 1996.

* cited by examiner

*Primary Examiner* — Venkataraman Balasubramanian
(74) *Attorney, Agent, or Firm* — Dickstein Shapiro LLP

(57) ABSTRACT

Conformationally constrained compounds that are novel and mimic the secondary structure of reverse-turn regions of biologically active peptides and proteins and having bicyclic frame-work are disclosed, as well as their prodrugs. Such reverse-turn mimetic structures and prodrugs have utility over a wide range of fields, including use as diagnostic and therapeutic agents. The invention also relates to the use of such compounds for the preparation of a medicament for treating or preventing cancer including an acute myeloid leukemia.

4 Claims, 3 Drawing Sheets

(A) Compound A (B) Compound B (A) Compound A (B) Compound C ered by Obrecht (Advances in Med. Chem., 4, 1-68, 1999).
COMPOUNDS OF REVERSE TURN MIMETICS AND THE USE THEREOF (2)

CROSS-REFERENCE TO RELATED APPLICATIONS

This application is a national stage application under 35 U.S.C. §371 of PCT/KR2008/006071, filed Oct. 15, 2008, which claims priority to U.S. application Ser. No. 11/974,941, filed Oct. 15, 2007, now U.S. Pat. No. 7,671,054.

TECHNICAL FIELD

The present invention relates generally to novel compounds of reverse-turn mimetics and their application in the treatment of medical conditions, e.g., cancer diseases, and pharmaceutical compositions comprising the mimetics.

BACKGROUND ART

Random screening of molecules for possible activity as therapeutic agents has occurred for many years and resulted in a number of important drug discoveries. While advances in molecular biology and computational chemistry have led to increased interest in what has been termed "rational drug design," such techniques have not proven as fast or reliable as initially predicted. Thus, in recent years there has been a renewed interest and return to random drug screening. To this end, particular strides having been made in new technologies based on the development of combinatorial chemistry libraries, and the screening of such libraries in search for biologically active members.

Initially, combinatorial chemistry libraries were generally limited to members of peptide or nucleotide origin.

While combinatorial libraries containing members of peptide and nucleotide origin are of significant value, there is still a need in the art for libraries containing members of different origin. For example, traditional peptide libraries to a large extent merely vary the amino acid sequence to generate library members. While it is well recognized that the secondary structures of peptides are important to biological activity, such peptide libraries do not impart a constrained secondary structure to its library members.

To this end, some researchers have cyclized peptides with disulfide bridges in an attempt to provide a more constrained secondary structure (Tumelty et al., J. Chem. Soc. 1067-68, 1994; Eichler et al., Peptide Res. 7:300-306, 1994). However, such cyclized peptides are generally still quite flexible and are poorly bioavailable, and thus have met with only limited success.

More recently, non-peptide compounds have been developed which more closely mimic the secondary structure of reverse-turns found in biologically active proteins or peptides. For example, U.S. Pat. No. 5,440,013 to Kahn and published PCT Applications Nos. WO94/03494, WO01/00210A1, and WO01/16135A2 to Kahn each disclose conformationally constrained, non-peptidic compounds, which mimic the three-dimensional structure of reverse-turns. In addition, U.S. Pat. No. 5,929,237 and its continuation-in-part U.S. Pat. No. 6,013,458, both to Kahn, disclose conformationally constrained compounds which mimic the secondary structure of reverse-turn regions of biologically active peptides and proteins. The synthesis and identification of conformationally constrained, reverse-turn mimetics and their application to diseases were well reviewed by Obrecht (Advances in Med. Chem., 4, 1-68, 1999).

While significant advances have been made in the synthesis and identification of conformationally constrained, reverse-turn mimetics, there remains a need in the art for small molecules which mimic the secondary structure of peptides. There is also a need in the art for libraries containing such members, as well as techniques for synthesizing and screening the library members against targets of interest, particularly biological targets, to identify bioactive library members.

In the mean time, a proto-oncogene is a normal gene that can become an oncogene due to mutations or increased expression. c-Myc (MYC) is known as one of the proto-oncogenes, and dysregulation of c-Myc is considered one of a series of oncogenic events required for mammalian tumorigenesis (Pelengaris S, Khan M. The many faces of c-MYC. Arch Biochem Biophys. 2003; 416:129-136). MYC dysregulation, via a variety of mechanisms, was also found to be associated with myeloid leukemias (Hoffman B, Amanullah A, Shafarenko M, Liebermann D A. The proto-oncogene c-myc in hematopoietic development and leukemogenesis. Oncogene. 2002; 21: 3414-3421). In addition, c-Myc was found to rapidly induce acute myeloid leukemia (Hui Luo et al. "c-Myc rapidly induces acute myeloid leukemia in mice without evidence of lymphoma-associated antiapoptotic mutations," Blood, 1 Oct. 2005, volume 106, Number 7, pp 2452-2461).

As c-Myc can be upregulated in acute myeloid leukemia, the oncogenic function of c-Myc has been studied and its exact role in myeloid leukemogenesis has been studied. Recently, some scientist found that Myc preferentially stimulated the growth of myeloid progenitor cells in methylcellulose and showed that Myc is a critical downstream effector of myeloid leukemogenesis (ibid.).

The finding that c-Myc plays a critical role in myeloid leukemogenesis indicates that by inhibiting an activation of c-Myc protein, an acute myeloid leukemia can be cured or prevented.

On the other hand, enzymes of the cytochrome P450 (CYP) superfamily are the major determinants of half-life and execute pharmacological effects of many therapeutic drugs. The human cytochrome P450 (CYP) 3A subfamily, includes CYP3A4, which is most abundant in the human liver (~40%) and metabolizes more than 50% of clinically used drugs (Shimada et al 1994; Rendic and Di Carlo 1997).

Due to the key role of CYP3A4 in drug metabolism, significant inactivation of this enzyme could result in marked pharmacokinetic drug-drug interactions. Inhibition of CYP3A4 may cause severe drug toxicity through the enhanced exposure to coadministered drugs (Dresser et al 2000). For example, when irreversible CYP3A4 inhibitors such as erythromycin or clarithromycin are coadministered with terfenadine, astemizole, or pimozide patients may experience Torsades de pointes (a life-threatening ventricular arrhythmia associated with QT prolongation) (Spinler et al 1995; Dresser et al 2000). Cancer patients, at times, undergo multiple treatment regimes, which increases the risk of drug-drug interactions followed by adverse drug reactions.

Therefore, in developing therapeutic agents, especially when it is to be administered in combination with other drugs, there is a need for providing compounds having less CYP3A4 inhibitory activity.

DISCLOSURE OF INVENTION

Technical Problem

The object of the present invention is to provide novel compounds which mimic the secondary structure of reverse-turn regions of biologically active peptides and proteins and have biological activity such as anti-cancer effect.

Another object of the present invention is to provide novel compounds which inhibit Wnt signaling.

Yet another object of the present invention is to provide novel compounds which can be used as pharmaceuticals, in particular having less CYP3A4 inhibitory activity (higher IC50).

Yet another object of the present invention is to provide novel compounds for a treatment or a prevention of acute myeloid leukemia through downregulation of expression of c-Myc.

Technical Solution

The present invention is directed to a new type of conformationally constrained compounds and derivatives including prodrugs thereof, which mimic the secondary structure of reverse-turn regions of biologically active peptides and proteins. This invention also discloses libraries containing such compounds, as well as the synthesis and screening thereof.

The compounds of the present invention have the following general Formula (I):

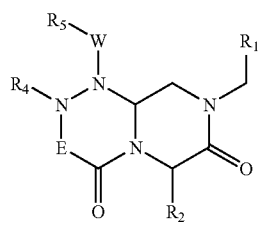

(I)

wherein E is —$ZR_3$— or —(C=O)—, wherein Z is CH or N; W is —(C=O)NH—, —(C=O)O—, —(C=O)S—, —S(O)$_2$— or a bond; and each of $R_1$, $R_2$, $R_3$, $R_4$ and $R_5$ is the same or different and independently an amino acid side chain moiety or an amino acid side chain derivative. The reverse turn mimetic compound may be present as an isolated stereoisomer or a mixture of stereoisomers or as a pharmaceutically acceptable salt thereof.

In certain embodiments, $R_1$ of compounds of Formula (I) is benzotriazolyl or substituted benzotriazolyl.

Specific examples of $R_1$, $R_2$, $R_3$, $R_4$ and $R_5$ are provided in the following detailed description.

In an embodiment wherein E is $CHR_3$, the compounds of this invention have the following Formula (II):

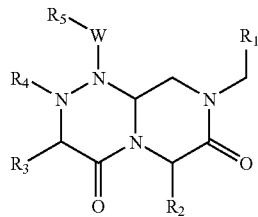

(II)

wherein W is as defined above, and $R_1$, $R_2$, $R_3$, $R_4$ and $R_5$ are as defined in the following detailed description.

In certain embodiments, the compounds of this invention have the following general Formula (III):

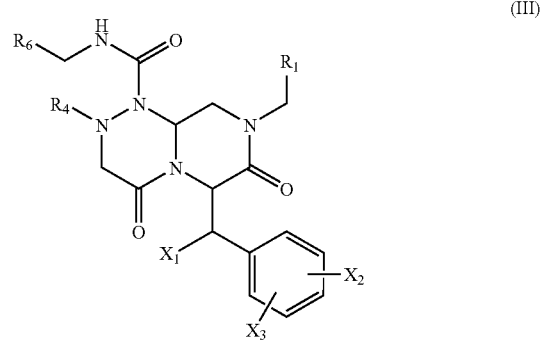

(III)

wherein $R_1$, $R_4$, $R_6$, $X_1$, $X_2$, and $X_3$ are defined in the following detailed description.

The present invention is also related to prodrugs using the libraries containing one or more compounds of Formula (I). A prodrug is typically designed to release the active drug in the body during or after absorption by enzymatic and/or chemical hydrolysis. The prodrug approach is an effective means of improving the oral bioavailability or i.v. administration of poorly water-soluble drugs by chemical derivatization to more water-soluble compounds. The most commonly used prodrug approach for increasing aqueous solubility of drugs containing a hydroxyl group is to produce esters containing an ionizable group; e.g., phosphate group, carboxylate group, alkylamino group (Fleisher et al., *Advanced Drug Delivery Reviews*, 115-130, 1996; Davis et al., *Cancer Res.*, 7247-7253, 2002, Golik et al., *Bioorg. Med. Chem. Lett.*, 1837-1842, 1996).

Examples of the functional group which may be released in the body may include phosphate,

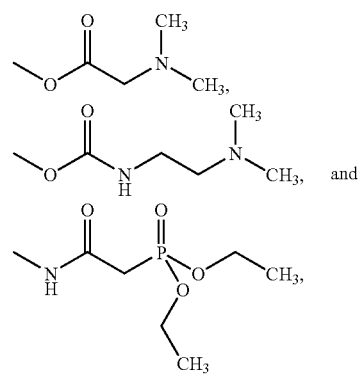

and

but any other functional groups that are conventionally used as the ionizable group in a prodrug can be used.

In certain embodiments, the prodrugs of the present invention have the following general Formula (IV):

(III)-$R_7$      (IV)

wherein (III) is Formula (III) as described above; one of $R_1$, $R_4$, $R_6$, $X_1$, $X_2$, and $X_3$ is linked to $R_7$ via Y; Y is an oxygen, sulfur, or nitrogen in $R_1$, $R_4$, or $R_6$, or an oxygen in $X_1$, $X_2$, or $X_3$; and $R_7$ is hydroxyalkyl, glycosyl, phosphoryloxymethyloxycarbonyl, substituted or unsubstituted piperidine carbonyloxy, or a salt thereof; or Y—$R_7$ is an amino acid residue, a combination of amino acid residues, phosphate, hemimalate, hemisuccinate, dimethylaminoalkylcarbamate, dimethylaminoacetate, or a salt thereof; and when not linked to $R_7$: $R_1$, $R_4$, $R_6$, $X_1$, $X_2$, and $X_3$ are defined in the following detailed description.

In certain embodiments, the prodrugs of the present invention are capable of serving as a substrate for a phosphatase, a carboxylase, or other enzymes and are thereby converted to compounds having general Formula (III).

The present invention is also directed to libraries containing one or more compounds of Formula (I) above, as well as methods for synthesizing such libraries and methods for screening the same to identify biologically active compounds.

In a related aspect, the present invention further provides novel compounds which have less CYP3A4 inhibitory activity. The present invention also provides novel compounds which have inhibition activity against Wnt signaling. The present invention also provides novel compounds which can be used for the preparation of a medicament for a treatment or a prevention of acute myeloid leukemia.

Advantageous Effects

The present invention provides novel compounds of reverse-turn mimetics. The compounds of the present invention exhibit less CYP3A4 inhibitory activity (higher IC50) which allows the compounds as potential pharmaceuticals, especially when it is to be administered in combination with other drugs. The compounds of the present invention showed strong inhibition activity against Wnt signaling and the compounds inhibited the growth of AML cancer cells and it can be used in the treatment or prevention of an acute myeloid leukemia.

BRIEF DESCRIPTION OF THE DRAWING

Reference will now be made in detail to the preferred embodiment of the present invention, examples of which are illustrated in the drawings attached herein. The embodiments are described below so as to explain the present invention by referring to the figures.

BEST MODE FOR CARRYING OUT THE INVENTION

Figure 1:
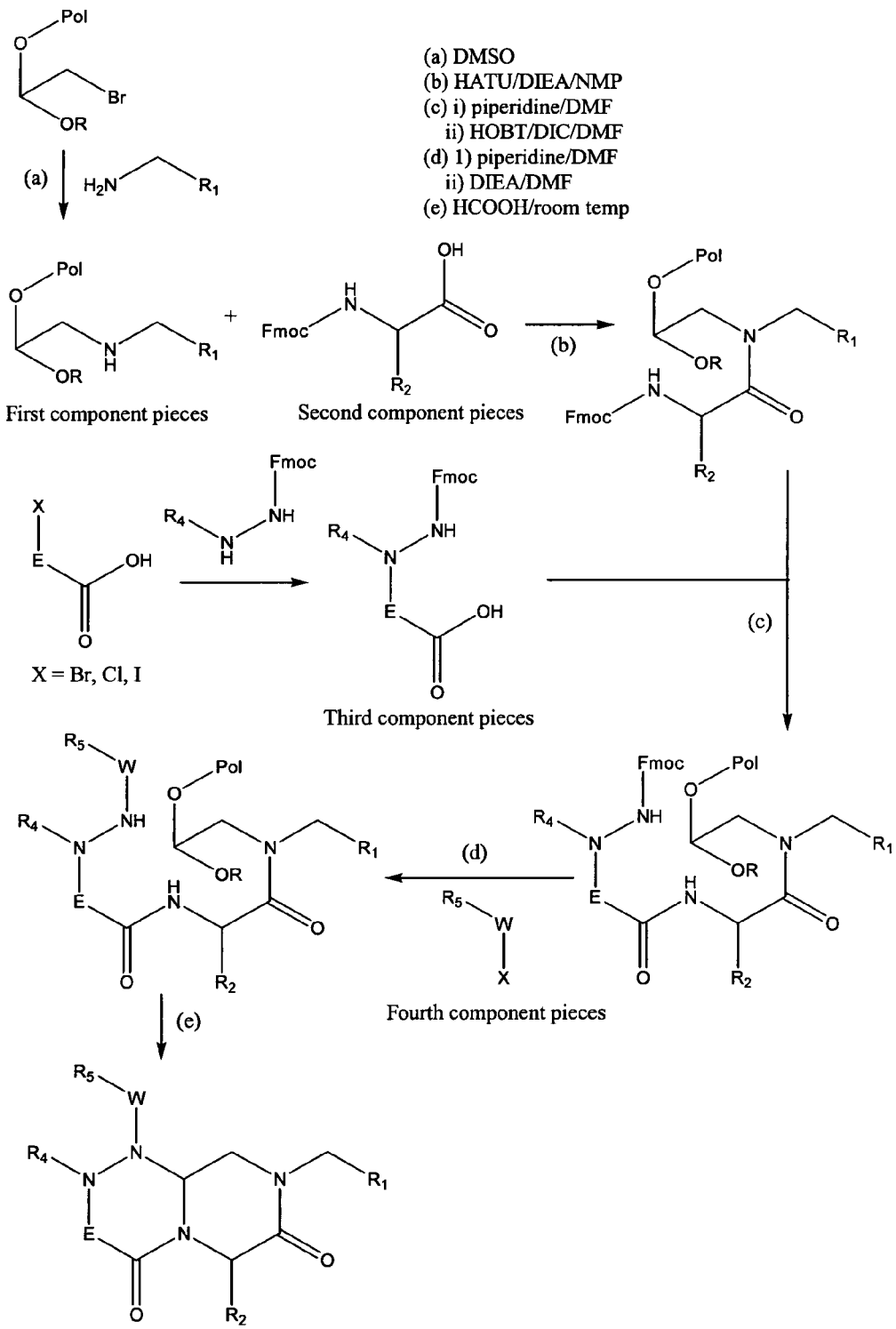
FIG. 1 provides a general synthetic scheme for preparing revers-turn mimetics of the present invention.

As used in the specification and appended claims, unless specified to the contrary, the following terms have the meaning indicated:

"Amino" refers to the —$NH_2$ radical.

"Amidino" refers to the —C(=NH)—$NH_2$ radical. One or both hydrogens of the amine group of the amidino may be replaced with one or two alkyl groups, as defined herein. The alkyl-derivatized amidino radicals are also referred to as "alkylamidino" and "dialkylamidino," respectively.

"Cyano" refers to the —CN radical.

"Carboxy" refers to the —COOR radical, wherein R is hydrogen or alkyl, as defined herein.

"Acyl" refers to the —COR radical, wherein R is alkyl, aryl, cycloalkyl, heterocyclyl, as defined herein. For example, R can be methyl, butenyl, cyclopropyl, and the like. The alkyl or aryl can be optionally substituted with the substituents as described for an alkyl or an aryl group, respectively. Exemplary acyl groups include, without limitation, phenylacyl, benzylacyl, $C_{1-6}$acyl (e.g., acetyl) and the like.

"Alkylsulfonate" refers to —$S(O)_2$—OR radical, wherein R is alkyl, as defined herein.

"Amidosulfonate" refers to the radical —$OS(O)_2$—$NR_2$, each R is independently hydrogen or alkyl. Exemplary amidosulfonates include —$OS(O)_2NH_2$, —$OS(O)_2NHMe$.

"Aminocarbonyl" refers to the radical —$C(O)NR_2$, each R is independently hydrogen, alkyl, amino, cycloalkylalkyl, heterocyclyl, alkoxyalkyl, hydroxyalkyl, hydroxyl, alkoxy, arylalkyl, heterocyclylalkyl, or two Rs together with the nitrogen atom to which they are attached form a heterocyclyl, as defined herein. When one of the R is hydrogen, the other R is C1-4alkyl, aminocarbonyl can be represented by "$C_{1-4}$alkylformamidyl."

"N-formamidyl" refers to the radical —NHC(O)H.

"Phenylsulfonyl" refers to the —$S(O)_2$—R radical, wherein R is phenyl, the phenyl can be further substituted with alkyl or chloro.

"Phenylsulfonate" refers to the —O—$S(O)_2$—R radical, wherein R is phenyl, the phenyl can be further substituted with alkyl or chloro.

"Alkylsulfonyl" refers to the —$S(O)_2$—R radical, wherein R is alkyl, as defined herein. Exemplary alkylsulfonyl radicals include methylsulfonyl.

"Alkylthio" refers to the —SR radical wherein R is alkyl, as defined herein.

"Arylthio" refers to the —SR radical wherein R is aryl, as defined herein. The aryl group of the arylthio can be further substituted with alkyl or chloro.

"Aryloxy" refers to the —OR radical wherein R is aryl, as defined herein. The aryl group can be further substituted with alkyl, alkoxy and the like.

"Acyloxyalkyl" refers to the —R'—OC(O)—R radical, wherein R is alkyl, aryl, cycloalkyl, heterocyclyl, as defined herein; and R' is an alkyl.

"Guanidino" refers to the —NH—C(=NH)—$NH_2$ radical. One or both hydrogens of the amine group of the guanidino may be replaced with one or two alkyl groups, as defined herein. The alkyl-derivatized guanidine radicals are also referred to as "alkylguanidino" and "dialkylguanidino," respectively.

"Nitro" refers to the —$NO_2$ radical.

"Alkyl" refers to a straight or branched hydrocarbon chain radical consisting solely of carbon and hydrogen atoms. An alkyl may be saturated (containing carbons linked together by single bonds only) or unsaturated (containing carbons linked together by at least one double bond or triple bond.) An alkyl having one to twelve carbon atoms is also referred to as "lower chain alkyl moieties" and can be presented by "$C_{1-12}$alkyl." In other embodiments, an alkyl may comprise one to four carbon atoms and be represented by "$C_{1-4}$alkyl." In other embodiments, an alkyl may comprise two to five carbon atoms and be represented by "$C_{2-5}$alkyl." An alkyl is attached to the rest of the molecule by a single bond. Examples of saturated alkyls include, without limitation, methyl, ethyl, n-propyl, 1-methylethyl (iso-propyl), n-butyl, n-pentyl, 1,1-dimethylethyl (t-butyl), 3-methylhexyl, 2-methylhexyl, and the like. Examples of unsaturated alkyls include, without limitation, ethenyl (i.e., vinyl), prop-1-enyl (i.e., allyl), but-1-enyl, pent-1-enyl, penta-1,4-dienyl, ethynyl (i.e., acytylenyl), prop-1-ynyl and the like.

An alkyl may also be a monocyclic or bicyclic hydrocarbon ring radical, which may include fused or bridged ring systems. A cyclic alkyl is also referred to as "cycloalkyl." In certain embodiments, a cycloalkyl may comprise three to six carbon atoms and be represented by "$C_{3-6}$cycloalkyl." Examples of monocyclic cycloalkyl radicals include, e.g., cyclopropyl, cyclobutyl, cyclopentyl, cyclohexyl, cycloheptyl, and cyclooctyl. An unsaturated cycloalkyl contains an endo double bond (i.e., a double bond in the ring). Examples of an unsaturated cycloalkyl include cyclohexenyl. Examples of bicyclic cycloalkyl radicals include, for example, norbornyl (i.e., bicyclo[2.2.1]heptyl), 7,7-dimethyl-bicyclo[2.2.1]heptyl, and the like.

Unless stated otherwise specifically in the specification, the term "alkyl" is meant to include both alkyl and "substituted alkyl," which refers to an alkyl radical in which one or more hydrogen atoms are replaced by one or more substituents independently selected from: acyl, amidino, alkylamidino, dialkylamidino, alkoxy, aryl, cyano, cycloalkyl, guanidino, alkylguanidino, dialkylguanidino, halo, heterocyclyl, hydrazinyl, hydroxyl, nitro, —OC(O)—$R^{11}$, —N($R^{15}$)$_2$, —C(O)O$R^{11}$, —C(O)N($R^{11}$)$_2$, —N($R^{11}$)C(O)O$R^{11}$, —N($R^{11}$)C(O)$R^{11}$, —N($R^{11}$)S(O)$_t$$R^{11}$ (where t is 1 or 2), —S(O)$_t$O$R^{11}$ (where t is 1 or 2), —S(O)$_p$$R^{11}$ (where p is 0, 1 or 2), and —S(O)$_t$N($R^{11}$)$_2$ (where t is 1 or 2) where each $R^{11}$ is independently hydrogen, alkyl, aryl, arylalkyl, heterocyclyl or heterocyclylalkyl, as defined herein.

"Alkoxy" refers to a radical represented by the formula alkyl-O—, wherein alkyl is as defined herein. The alkyl portion can be further substituted by one or more halogen. An alkoxy may also be represented by the number of the carbons in the alkyl group, for example, $C_{1-6}$alkoxy or $C_{1-3}$alkoxy.

"Aryl" refers to a radical derived from an aromatic monocyclic or bicyclic ring system by removing a hydrogen atom from a ring carbon atom. The aromatic monocyclic or bicyclic hydrocarbon ring system comprises six to twelve carbon atoms (i.e., $C_{6-12}$aryl), wherein at least one of the rings in the ring system is fully unsaturated, i.e., it contains a cyclic, delocalized (4n+2) π-electron system in accordance with the Hückel theory. Optionally, one or two ring atoms of the aryl may be heteroatoms selected from nitrogen, oxygen or sulfur. Examples of aryl radicals include, but are not limited to, phenyl and naphthyl. Unless stated otherwise specifically in the specification, the term "aryl" is meant to include both aryl and "substituted aryl," which refers to an aryl radical in which one or more hydrogen atoms are replaced by one or more substituents independently selected from: alkyl, acyl, amidino, amidosulfonate, alkoxy, aryloxy, cyano, guanidino, alkylguanidino, dialkylguanidino, halo, hydrazinyl, hydroxyl, nitro, heterocyclyl, —OC(O)—$R^{11}$, —N($R^{11}$)$_2$, —C(O)O$R^{11}$, —C(O)N($R^{11}$)$_2$, —N($R^{11}$)C(O)O$R^{11}$, —N($R^{11}$)C(O)$R^{11}$, —N($R^{11}$)S(O)$_t$$R^{11}$ (where t is 1 or 2), —S(O)$_p$O$R^{11}$ (where t is 1 or 2), —S(O)$_p$$R^{11}$ (where p is 0, 1 or 2), and —S(O)$_t$N($R^{11}$)$_2$ (where t is 1 or 2) where each $R^{11}$ is independently hydrogen, alkyl, aryl, arylalkyl, heterocyclyl or heterocyclylalkyl.

"Arylalkyl" refers to an alkyl radical wherein one or more hydrogens of the alkyl are replaced with one or more aryl groups, as defined herein. In various embodiments, arylalkyls include from 7 to 15 carbons and can be represented by $C_{7-15}$arylalkyl. In certain embodiments, arylalkyl is aryl$C_{1-4}$alkyl wherein a $C_{1-4}$alkyl is substituted with one aryl or two aryl groups, the latter being also referred to as "diarylalkyl" or "bisarylalkyl". Examples of aryl$C_{1-4}$alkyl include, but are not limited to arylmethyl, arylethyl, arylpropyl, arylbutyl, bisarylmethyl, bisarylethyl, bisarylpropyl, bisarylbutyl. Exemplary arylalkyl radicals include, without limitation, benzyl, naphthylmethyl, diphenylmethyl, 3,3-bisphenylpropyl and the like. Unless stated otherwise specifically in the specification, the term "arylalkyl" is meant to include both arylalkyl and "substituted arylalkyl," wherein the alkyl part and/or the aryl part of the arylalkyl radical may be substituted as described herein for the alkyl radical and aryl radical, respectively.

"Cycloalkylalkyl" refers to an alkyl radical wherein one or more hydrogens of the alkyl are replaced with one or more c groups, as defined herein. In certain embodiments, cycloalkylalkyl is cycloalkyl$C_{1-2}$alkyl such as cycloalkylmethyl, cycloalkylethyl and the like. Exemplary cycloalkylalkyl radicals include, without limitation, cyclohexylalkyl (e.g., cyclohexylmethyl and cyclohexylethyl) and cyclopentylalkyl (e.g., cyclopentylmethyl and cyclopentylethyl) and the like. Unless stated otherwise specifically in the specification, the term "cycloalkylalkyl" is meant to include both cycloalkylalkyl and "substituted cycloalkylalkyl," wherein the alkyl part and/or the cycloalkyl part of the cycloalkylalkyl radical may be substituted as described herein for the alkyl radical and cycloalkyl radical, respectively.

"Glycosyl" refers to a radical by removing the hemiacetal hydroxyl group from a cyclic form of a monosaccharide (e.g., glucose), disaccharide, oligosaccharide (comprising three to ten monosaccharides), or polysaccharide (comprising more than ten monosaccharides).

"Halo" or "halogen" refers to fluoro, chloro, bromo or iodo radicals.

"Haloalkyl" refers to an alkyl radical, as defined herein, which is substituted by one or more halo radicals, as defined herein. Exemplary haloalkyls include, without limitation: trifluoromethyl, difluoromethyl, trichloromethyl, 2,2,2-trifluoroethyl, 1-fluoromethyl-2-fluoroethyl, 3-bromo-2-fluoropropyl, 1-bromomethyl-2-bromoethyl, and the like. An alkyl substituted with one or more fluoro is also referred to as "perfluoroalkyl," for example, "perfluo$C_{1-4}$alkyl." The alkyl part of the haloalkyl radical may be optionally substituted as defined herein for an alkyl group.

"Heterocyclyl" refers to a stable heterocyclic ring radical that comprises two to eleven carbon atoms and from one to three heteroatoms selected from nitrogen, oxygen and sulfur. In certain embodiments, the heterocyclyl contains one or two heteroatoms. Unless stated otherwise specifically in the specification, the heterocyclyl radical may be a monocyclic or bicyclic ring system, which may include fused or bridged ring systems. In certain embodiments, the heterocyclyl may be a 5-, 6- or 7-membered monocyclic ring. In other embodiments, the heterocyclyl may be an 8-, 9-, 10- 11- or 12-membered fused bicyclic ring. The heteroatoms in the heterocyclyl radical may be optionally oxidized. One or more nitrogen atoms, if present, may be optionally quaternized. The heterocyclyl radical may be non-aromatic or aromatic (i.e., at least one ring in the heterocyclyl radical has a delocalized (4n+2) π-electron system in accordance with the Hückel theory.) The heterocyclyl may be attached to the rest of the molecule through any atom of the ring(s). Examples of non-aromatic heterocyclyl radicals include, but are not limited to, dioxolanyl, decahydroisoquinolyl, imidazolinyl, imidazolidinyl, isothiazolidinyl, isoxazolidinyl, morpholinyl, octahydroindolyl, octahydroisoindolyl, 2-oxopiperazinyl, 2-oxopiperidinyl, 2-oxopyrrolidinyl, oxazolidinyl, piperidinyl (also referred to as "piperidyl"), piperazinyl, 4-piperidonyl, 3-pyrrolinyl, pyrrolidinyl, pyrazolidinyl, quinuclidinyl, thiazolidinyl, tetrahydrofuryl, trithianyl, tetrahydropyranyl, thiomorpholinyl, and thiamorpholinyl. Examples of aromatic heterocyclyl radicals include, but are not limited to, azepinyl, acridinyl, benzimidazolyl, benzindolyl, 1,3-benzodioxolyl, benzofuranyl, benzooxazolyl, benzoisoxazolyl, benzo[d]thiazolyl, benzothiadiazolyl, benzo[b][1,4]dioxepinyl, benzo[b][1,4]oxazinyl, 1,4-benzodioxanyl, benzoxazolyl, benzodioxolyl, benzodioxinyl, benzopyranyl, benzopyrazolyl, benzofuranyl, benzofuranonyl, benzothienyl (benzothiophenyl), benzothieno[3,2-d]pyrimidinyl, benzotriazolyl, carbazolyl, chromone, cinnolinyl, cyclopenta[d]pyrimidinyl, dibenzofuranyl, dibenzothiophenyl, furanyl, furanonyl, furo[3,2-c]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6,6a,7,8,9,10,10a-octahydrobenzo[h]quinazolinyl, phenazinyl, phenothiazinyl, phenoxazinyl, phthalazinyl, pteridinyl, purinyl, pyrrolyl, pyrazolyl, pyrazolo[3,4-d]pyrimidinyl, pyridinyl (also referred to as pyridyl), pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 1,2,3,4-tetrahydrocarbazolyl, 5,6,7,8-tetrahydroquinazolinyl, thiazolyl, thiadiazolyl, triazolyl, tetrazolyl, triazin-2-yl, thieno[2,3-d]pyrimidinyl, thieno[3,2-d]pyrimidinyl, thieno[2,3-c]pridinyl, and thiophenyl (i.e. thienyl). Unless stated otherwise specifically in the specification, the term "heterocyclyl" is meant to include both heterocyclyl and "substituted heterocyclyl," which refers to a heterocyclyl radical substituted by one or more substituents selected from alkyl, acyl, oxo (e.g., pyridinonyl, pyrrolidonyl), aryl, arylalkyl, acyloxyalkyl, amidino, alkoxy, cyano, guanidino, alkylguanidino, dialkylguanidino, halo, hydrazinyl, hydroxyl, nitro, —OC(O)—$R^{11}$, —N$(R^{11})_2$, —C(O)O$R^{11}$, —C(O)N$(R^{11})_2$, —N$(R^{11})$C(O)O$R^{11}$, —N$(R^{11})$C(O)$R^{11}$, —N$(R^{11})$S(O)$_t R^{11}$ (where t is 1 or 2), —S(O)$_t$O$R^{11}$ (where t is 1 or 2), —S(O)$_p R^{11}$ (where p is 0, 1 or 2), and —S(O)$_t$N$(R^{11})_2$ (where t is 1 or 2) where each $R^{11}$ is independently hydrogen, alkyl, aryl, arylalkyl, heterocyclyl or heterocyclylalkyl.

"Heterocyclylalkyl" refers to an alkyl radical wherein one or more hydrogens of the alkyl are replaced with one or more heterocyclyl groups, as defined herein. If the heterocyclyl is a nitrogen-containing heterocyclyl, the heterocyclyl may be attached to the alkyl radical at the nitrogen atom. In certain embodiments, the alkyl part of the heterocyclylalkyl contains 1-4 carbon atoms and can be represented by heterocyclylC$_{1-4}$alkyl. Examples of heterocyclylalkyl radicals include, without limitation, morpholinylalkyl such as morpholinylmethyl, piperidylalkyl such as piperidylmethyl, imidazolidinylalkyl such as imidazolidinylmethyl and the like. Additional examples of heterocyclylalkyl radicals, wherein the heterocyclyl part is aromatic, include, but are not limited to: pyridylmethyl, pyridylethyl, pyridylpropyl, pyridylbutyl, quinolinylmethyl, quinolinylethyl, quinolinylpropyl, quinolinylbutyl, indazolylmethyl, indazolylethyl, indazolylpropyl, indazolylbutyl, benzpyrazolylmethyl, benzpyrazolylethyl, benzpyrazolylpropyl, benzpyrazolylbutyl, isoquinolinylmethyl, isoquinolinylethyl, isoquinolinylpropyl, isoquinolinylbutyl, benzotriazolylmethyl, benzotriazolylethyl, benzotriazolylpropyl, benzotriazolylbutyl and the like. Unless stated otherwise specifically in the specification, the term "heterocyclylalkyl" is meant to include both heterocyclylalkyl and "substituted heterocyclylalkyl," wherein the alkyl part and/or the heterocyclyl part of the heterocyclylalkyl radical may be substituted as described herein for the alkyl radical and the heterocyclyl radical, respectively.

The compounds, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. When the compounds described herein contain olefinic double bonds or other centers of geometric asymmetry, and unless specified otherwise, it is intended that the compounds include both E and Z geometric isomers (e.g., cis or trans.) Likewise, all possible isomers, as well as their racemic and optically pure forms, and all tautomeric forms are also intended to be included.

As used herein, "amino acid" is meant to include naturally occurring α-amino acids and/or unnatural amino acids, such as β-amino acids and homoamino acids. Examples of the amino acids include, but are not limited to: alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine and 3,5-diiodotyrosine.

"Amino acid residue" or "amino acid side chain moiety" refers to the portion of an amino acid that remains after losing a water molecule (or alcohol) when the amino acid is condensed with a molecule. Typically, an amino acid is condensed with a molecule, including a compound of any of Formulae (I)-(IV), by forming a peptide bond. In certain embodiments, the amino functional group of the amino acid can be condensed with a carboxylic acid group or its reactive equivalent (e.g., carboxylic anhydride) of the molecule. In other embodiments, the carboxylic acid functional group of the amino acid can be condensed with an amine group of the molecule. Typically, a molecule of water is lost during the formation of the peptide bond. Examples of the "amino acid residues" or "amino acid side chain moiety" include, but are not limited to, residues of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine, valine, phosphoserine, phosphothreonine, phosphotyrosine, 4-hydroxyproline, hydroxylysine, demosine, isodemosine, gamma-carboxyglutamate, hippuric acid, octahydroindole-2-carboxylic acid, statine, 1,2,3,4-tetrahydroisoquinoline-3-carboxylic acid, penicillamine, ornithine, 3-methylhistidine, norvaline, beta-alanine, gamma-aminobutylic acid, cirtulline, homocysteine, homoserine, methyl-alanine, para-benzoylphenylalanine, phenylglycine, propargylglycine, sarcosine, methionine sulfone, tert-butylglycine, 3,5-dibromotyrosine, 3,5-diiodotyrosine, glycosylated threonine, glyclosylated serine, and glycosylated asparagine.

An "amino acid side chain derivative" refers to a derivative of any of the amino acid side chain moiety as described in Table 1. In certain embodiments, the amino acid side chain derivative is alkyl, acyl, alkoxy, aryl, arylalkyl, heterocyclyl, or heterocyclylalkyl, as defined herein.

TABLE 1

| Amino Acid Side Chain Moiety | Amino Acid |
| --- | --- |
| —H | Glycine |
| —CH$_3$ | Alanine |
| —CH(CH$_3$)$_2$ | Valine |
| —CH$_2$CH(CH$_3$)$_2$ | Leucine |
| —CH(CH$_3$)CH$_2$CH$_3$ | Isoleucine |
| —(CH$_2$)$_4$NH$_3^+$ | Lysine |
| —(CH$_2$)$_3$NHC(NH$_2$)NH$_2^+$ | Arginine |
| 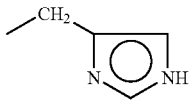 | Histidine |
| —CH$_2$COO$^-$ | Aspartic acid |
| —CH$_2$CH$_2$COO$^-$ | Glutamic acid |
| —CH$_2$CONH$_2$ | Asparagine |
| —CH$_2$CH$_2$CONH$_2$ | Glutamine |
| 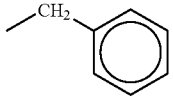 | Phenylalanine |
| 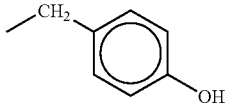 | Tyrosine |
| 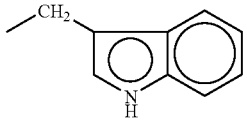 | Tryptophan |
| —CH$_2$SH | Cysteine |
| —CH$_2$CH$_2$SCH$_3$ | Methionine |
| —CH$_2$OH | Serine |
| —CH(OH)CH$_3$ | Threonine |
| 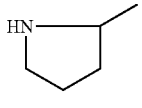 | Proline |
| 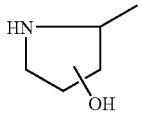 | Hydroxyproline |

A "stereoisomer" refers to a compound made up of the same atoms bonded by the same bonds but having different three-dimensional structures, which are not interchangeable. It is therefore contemplated that various stereoisomers and mixtures thereof and includes "enantiomers," which refers to two stereoisomers whose molecules are nonsuperimposable mirror images of one another.

A "tautomer" refers to a proton shift from one atom of a molecule to another atom of the same molecule.

"Prodrugs" is meant to indicate a compound that may be converted under physiological conditions or by solvolysis to a biologically active compound described herein. Thus, the term "prodrug" refers to a precursor of a biologically active compound that is pharmaceutically acceptable. A prodrug may be inactive when administered to a subject, but is converted in vivo to an active compound, for example, by hydrolysis. The prodrug compound often offers advantages of solubility, tissue compatibility or delayed release in a mammalian organism (see, Bundgard, H., Design of Prodrugs (1985), pp. 7-9, 21-24 (Elsevier, Amsterdam).

A discussion of prodrugs is provided in Higuchi, T., et al., "Pro-drugs as Novel Delivery Systems," A.C.S. Symposium Series, Vol. 14, and in Bioreversible Carriers in Drug Design, ed. Edward B. Roche, American Pharmaceutical Association and Pergamon Press, 1987, both of which are incorporated in full by reference herein.

The term "prodrug" is also meant to include any covalently bonded carriers, which release the active compound in vivo when such prodrug is administered to a mammalian subject. Prodrugs of an active compound, as described herein, may be prepared by modifying functional groups present in the active compound in such a way that the modifications are cleaved, either in routine manipulation or in vivo, to the parent active compound. Prodrugs include compounds wherein a hydroxyl, amino or mercapto group is bonded to any group that, when the prodrug of the active compound is administered to a mammalian subject, cleaves to form a free hydroxyl, free amino or free mercapto group, respectively. Examples of the prodrugs include, but are not limited to, acetate, succinate, phosphate, hemisuccinate, malate, hemimalate, formate and benzoate derivatives of alcohol or amine functional groups in the active compounds and the like. Other examples of the prodrugs include, but are not limited to, amino acid derivatives of alcohol or amine functional groups in the active compounds and the like.

The present invention is directed to conformationally constrained compounds that mimic the secondary structure of reverse-turn regions of biological peptide and proteins (also referred to herein as "reverse-turn mimetics," and is also directed to chemical libraries relating thereto.

The reverse-turn mimetic structures of the present invention are useful as bioactive agents, including (but not limited to) use as diagnostic, prophylactic and/or therapeutic agents. The reverse-turn mimetic structure libraries of this invention are useful in the identification of bioactive agents having such uses. In the practice of the present invention, the libraries may contain from tens to hundreds to thousands (or greater) of individual reverse-turn structures (also referred to herein as "members").

In one aspect of the present invention, a reverse-turn mimetic structure is disclosed having the following Formula (I):

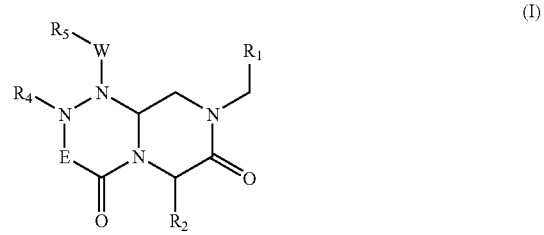

wherein E is —ZR$_3$— or —(C=O)—, wherein Z is CH or N; W is —(C=O)NH—, —(C=O)O—, —(C=O)S—, —S(O)$_2$— or a bond; and each of R$_1$, R$_2$, R$_3$, R$_4$ and R$_5$ is the same or different and independently an amino acid side chain moiety or an amino acid side chain derivative. The reverse turn mimetic compound may be present as an isolated stereoisomer or a mixture of stereoisomers or as a pharmaceutically acceptable salt thereof.

In certain embodiments, R$_1$ of compounds of Formula (I) is benzotriazolyl or substituted benzotriazolyl.

In certain embodiments, R$_1$ of compounds of Formula (I) may be benzotriazolyl or substituted benzotriazolyl having one or more substituents independently selected from $C_{1-7}$alkyl, carboxyalkyl, $C_{1-2}$alkyl-heterocyclylcarbonylalkyl, and aminocarbonyl.

In certain embodiment of the compounds described in the preceding paragraph, $C_{1-7}$alkyl is methyl.

In certain embodiments, $R_2$, $R_4$ and $R_5$ of compounds of Formula (I) are independently selected from the group consisting of:

$C_{1-12}$alkyl or substituted $C_{1-12}$alkyl having one or more substituents independently selected from: halogen, cyano, $C_{1-6}$alkoxy, amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{2-12}$alkenyl or substituted $C_{2-12}$alkenyl having one or more substituents independently selected from: amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{6-12}$aryl or substituted $C_{6-12}$aryl having one or more substituents independently selected from: halogen, amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{1-6}$alkoxy;

$C_{6-13}$heterocyclylalkyl, which has 1 to 2 heteroatoms selected from nitrogen, oxygen or sulfur, or substituted $C_{6-13}$heterocyclylalkyl which has 1 to 2 heteroatoms selected from nitrogen, oxygen or sulfur and has one or more substituents independently selected from: halogen, $C_{1-6}$alkyl, $C_{1-6}$alkoxy, cyano, and hydroxyl; and $C_{7-13}$arylalkyl or substituted $C_{7-13}$arylalkyl having one or more substituents independently selected from: amino, amidino, guanidino, hydrazino, $C_{1-4}$alkylamino, $C_{1-4}$dialkylamino, halogen, perfluoro $C_{1-6}$alkyl, $C_{1-6}$alkoxy, nitro, carboxy, cyano, sulfuryl and hydroxyl; and $R_3$ is selected from the group consisting of:
hydrogen;

$C_{1-12}$alkyl or substituted $C_{1-12}$alkyl having one or more substituents independently selected from: halogen, cyano, $C_{1-6}$alkoxy, amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{2-12}$alkenyl or substituted $C_{2-12}$alkenyl having one or more substituents independently selected from: amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{6-12}$aryl or substituted $C_{6-12}$aryl having one or more substituents independently selected from: halogen, amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{1-6}$alkoxy;

$C_{6-13}$heterocyclylalkyl, which has 1 to 2 heteroatoms selected from nitrogen, oxygen or sulfur, or substituted $C_{6-13}$heterocyclylalkyl which has 1 to 2 heteroatoms selected from nitrogen, oxygen or sulfur and has one or more substituents independently selected from: halogen, $C_{1-6}$alkyl, $C_{1-6}$alkoxy, cyano, and hydroxyl; and $C_{7-13}$arylalkyl or substituted $C_{7-13}$arylalkyl having one or more substituents independently selected from: amino, amidino, guanidino, hydrazino, $C_{1-4}$alkylamino, $C_{1-4}$dialkylamino, halogen, perfluoro $C_{1-6}$alkyl, $C_{1-6}$alkoxy, nitro, carboxy, cyano, sulfuryl and hydroxyl.

In certain embodiments, $R_2$, $R_4$ and $R_5$ of compounds of Formula (I) are independently selected from the group consisting of:

amino$C_{2-5}$alkyl; guanidino$C_{2-5}$alkyl; $C_{1-4}$alkylguanidino$C_{2-5}$alkyl, di$C_{1-4}$alkylguanidino-$C_{2-5}$alkyl; amidino$C_{2-5}$alkyl; $C_{1-4}$alkylamidino$C_{2-5}$alkyl; di$C_{1-4}$alkylamidino$C_{2-5}$alkyl; $C_{1-3}$alkoxy;

$C_{1-12}$alkyl; $C_{6-12}$aryl; $C_{6-12}$arylalkyl; $C_{2-12}$alkenyl;

phenyl or substituted phenyl having one or more substituents independently selected from: amino, amidino, guanidino, hydrazino, $C_{1-4}$alkylamino, $C_{1-4}$dialkylamino, halogen, perfluoro$C_{1-4}$alkyl, $C_{1-4}$alkyl, $C_{1-3}$alkoxy, nitro, carboxy, cyano, sulfuryl and hydroxyl;

naphthyl or substituted naphthyl having one or more substituents independently selected from: amino, amidino, guanidino, hydrazino, $C_{1-4}$alkylamino, $C_{1-4}$dialkylamino, halogen, perfluoro$C_{1-4}$alkyl, $C_{1-4}$alkyl, $C_{1-3}$alkoxy, nitro, carboxy, cyano, sulfuryl, and hydroxyl;

benzyl or substituted benzyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-3}$alkoxy, nitro, carboxy, cyano, sulfuryl and hydroxyl;

bisphenylmethyl or substituted bisphenylmethyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-3}$alkoxy, nitro, carboxy, cyano, sulfuryl and hydroxyl;

pyridyl or substituted pyridyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-3}$alkoxy, nitro, carboxy, cyano, sulfuryl and hydroxyl;

pyridyl$C_{1-4}$alkyl, or substituted pyridyl$C_{1-4}$alkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl;

pyrimidyl$C_{1-4}$alkyl, or substituted pyrimidyl$C_{1-4}$alkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl;

triazin-2-yl$C_{1-4}$alkyl, or substituted triazin-2-yl$C_{1-4}$alkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl;

imidazolyl$C_{1-4}$alkyl or substituted imidazolyl$C_{1-4}$alkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-5}$alkyl, $C_{1-3}$alkoxy, nitro, carboxy, cyano, sulfuryl and hydroxyl;

N-amidinopiperazinyl-N—$C_{0-4}$alkyl, N-amidinopiperidinyl$C_{1-4}$alkyl; and 4-aminocyclohexyl$C_{0-2}$alkyl; and $R_3$ is selected from the group consisting of:

hydrogen; amino$C_{2-5}$alkyl; guanidino$C_{2-5}$alkyl; $C_{1-4}$alkylguanidino$C_{2-5}$alkyl, di$C_{1-4}$alkylguanidino-$C_{2-5}$alkyl; amidino$C_{2-5}$alkyl; $C_{1-4}$alkylamidino$C_{2-5}$alkyl; di$C_{1-4}$alkylamidino$C_{2-5}$alkyl; $C_{1-3}$alkoxy;

$C_{1-12}$alkyl; $C_{6-12}$aryl; $C_{6-12}$arylalkyl; $C_{2-12}$alkenyl;

phenyl or substituted phenyl having one or more substituents independently selected from: amino, amidino, guanidino, hydrazino, $C_{1-4}$alkylamino, $C_{1-4}$dialkylamino, halogen, perfluoro$C_{1-4}$alkyl, $C_{1-4}$alkyl, $C_{1-3}$alkoxy, nitro, carboxy, cyano, sulfuryl and hydroxyl;

naphthyl or substituted naphthyl having one or more substituents independently selected from: amino, amidino, guanidino, hydrazino, $C_{1-4}$alkylamino, $C_{1-4}$dialkylamino, halogen, perfluoro$C_{1-4}$alkyl, $C_{1-4}$alkyl, $C_{1-3}$alkoxy, nitro, carboxy, cyano, sulfuryl, and hydroxyl;

benzyl or substituted benzyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-3}$alkoxy, nitro, carboxy, cyano, sulfuryl and hydroxyl;

bisphenylmethyl or substituted bisphenylmethyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-3}$alkoxy, nitro, carboxy, cyano, sulfuryl and hydroxyl;

pyridyl or substituted pyridyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-3}$alkoxy, nitro, carboxy, cyano, sulfuryl and hydroxyl;

pyridyl$C_{1-4}$alkyl, or substituted pyridyl$C_{1-4}$alkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl;

pyrimidyl$C_{1-4}$alkyl, or substituted pyrimidyl$C_{1-4}$alkyl having one or more substituents independently selected from: amino, amidino, guanidino, hydrazino, $C_{1-4}$alkylamino, $C_{1-4}$dialkylamino, halogen, perfluoro $C_1$ alkyl, $C_{1-4}$alkyl, $C_{1-3}$alkoxy, nitro, carboxy, cyano, sulfuryl and hydroxyl;

triazin-2-yl$C_{1-4}$alkyl, or substituted triazin-2-yl$C_{1-4}$alkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl;

imidazolyl$C_{1-4}$alkyl or substituted imidazolyl$C_{1-4}$alkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl;

N-amidinopiperazinyl-N—$C_{0-4}$alkyl, N-amidinopiperidinyl$C_{1-4}$alkyl; and 4-aminocyclohexyl$C_{0-2}$alkyl.

In certain embodiments, $R_1$ of compounds of Formula (I) may be benzotriazolyl or substituted benzotriazolyl having one or more substituents independently selected from methyl, carboxymethyl, morpholinylcarbonylmethyl, methylpiperazinyl-carbonylmethyl, $C_{1-7}$alkylaminocarbonylmethyl, $C_{1-4}$dialkylaminocarbonylmethyl, methoxyethylaminocarbonylmethyl, aminocarbonylmethyl, and pyridinylmethylaminocarbonylmethyl, but not limited thereto. Specific examples of $R_1$ include 1-methyl-1H-benzotriazolyl, 2-methyl-2H-benzotriazolyl, 1-ethoxycarbonylmethyl-1H-benzotriazolyl, 1-hydroxycarbonylmethyl-1H-benzotriazolyl, 1-morpholinyl-N-carbonylmethyl-1H-benzotriazolyl, 1-N-methylpiperazinyl-N-carbonylmethyl-1H-benzotriazolyl, 1-aminocarbonylmethyl-1H-benzotriazolyl, 1-methylaminocarbonylmethyl-1H-benzotriazolyl, and 1-pyrdinylmethylaminocarbonylmethyl-1H-benzotriazolyl.

In certain embodiments, $R_2$, $R_4$ and $R_5$ of compounds of Formula (I) are independently selected from the group consisting of:

$C_{1-12}$alkyl or substituted $C_{1-12}$alkyl having one or more substituents independently selected from acyl, carboxy, alkylthio, and phenylsulfonyl;

$C_{2-12}$alkenyl or substituted $C_{2-12}$alkenyl having one or more substituents independently selected from acyl, carboxy, alkylthio, and phenylsulfonyl;

substituted $C_{6-12}$aryl substituted with amidosulfonate;

aryl$C_{1-4}$alkyl or substituted aryl$C_{1-4}$alkyl having one or more substituents independently selected from: amino, amidino, guanidino, hydrazino, $C_{1-4}$alkylamino, $C_{1-4}$dialkylamino, $C_{3-6}$cycloalkyl, halogen, perfluoro$C_{1-4}$alkyl, $C_{1-6}$alkyl, $C_{1-3}$alkoxy, nitro, carboxy, cyano, sulfuryl, hydroxyl, $C_{1-6}$alkyloxy$C_{1-6}$acyl, morphorlinyl$C_{1-6}$alkyl, aryl, aryloxy, (alkyl)(arylalkyl)amino, heterocyclyl, acyl, amidosulfonate, aminocarbonyl, alkylsulfonate, alkylsulfonyl, alkylthio, arylthio, phenylsulfonate, phenylsulfonyl, morphorlinyl$C_{1-3}$alkoxy, N-formamidyl, and pyrrolidonyl;

heterocyclyl or substituted heterocyclyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-3}$alkoxy, nitro, carboxy, cyano, sulfuryl and hydroxyl;

heterocyclyl$C_{1-4}$alkyl or substituted heterocyclyl$C_{1-4}$alkyl having one or more substituents independently selected from: amino, amidino, guanidino, hydrazino, $C_{1-4}$alkylamino, $C_{1-4}$dialkylamino, $C_{3-6}$cycloalkyl, halogen, perfluoro$C_{1-4}$alkyl, $C_{1-6}$alkyl, $C_{1-3}$alkoxy, nitro, carboxy, cyano, sulfuryl, hydroxyl, $C_{1-6}$alkyloxy$C_{1-6}$acyl, morphorlinyl$C_{1-6}$alkyl, arylalkyl, aryl, heterocyclyl, acyl, phenylsulfonyl, cycloalkylalkyl, acyloxyalkyl, aminocarbonyl and $C_{1-4}$alkylformamidyl;

cycloalkyl or substituted cycloalkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl; and cycloalkylalkyl or substituted cycloalkylalkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl; and $R_3$ is selected from the group consisting of:

hydrogen;

$C_{1-12}$alkyl or substituted $C_{1-12}$alkyl having one or more substituents independently selected from acyl, carboxy, alkylthio, and phenylsulfonyl;

$C_{2-12}$alkenyl or substituted $C_{2-12}$alkenyl having one or more substituents independently selected from acyl, carboxy, alkylthio, and phenylsulfonyl;

substituted $C_{6-12}$aryl substituted with amidosulfonate;

aryl$C_{1-4}$alkyl or substituted aryl$C_{1-4}$alkyl having one or more substituents independently selected from: amino, amidino, guanidino, hydrazino, $C_{1-4}$alkylamino, $C_{1-4}$dialkylamino, $C_{3-6}$cycloalkyl, halogen, perfluoro$C_{1-4}$alkyl, $C_{1-6}$alkyl, $C_{1-3}$alkoxy, nitro, carboxy, cyano, sulfuryl, hydroxyl, $C_{1-6}$alkyloxy$C_{1-6}$acyl, morphorlinyl$C_{1-6}$alkyl, aryl, aryloxy, (alkyl)(arylalkyl)amino, heterocyclyl, acyl, amidosulfonate, aminocarbonyl, alkylsulfonate, alkylsulfonyl, alkylthio, arylthio, phenylsulfonate, phenylsulfonyl, morphorlinyl$C_{1-3}$alkoxy, N-formamidyl, and pyrrolidonyl;

heterocyclyl or substituted heterocyclyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-3}$alkoxy, nitro, carboxy, cyano, sulfuryl and hydroxyl;

heterocyclyl$C_{1-4}$alkyl or substituted heterocyclyl$C_{1-4}$alkyl having one or more substituents independently selected from: amino, amidino, guanidino, hydrazino, $C_{1-4}$alkylamino, $C_{1-4}$dialkylamino, $C_{3-6}$cycloalkyl, halogen, perfluoro$C_{1-4}$alkyl, $C_{1-6}$alkyl, $C_{1-3}$alkoxy, nitro, carboxy, cyano, sulfuryl, hydroxyl, $C_{1-6}$alkyloxy$C_{1-6}$acyl, morphorlinyl$C_{1-6}$alkyl, arylalkyl, aryl, heterocyclyl, acyl, phenylsulfonyl, cycloalkylalkyl, acyloxyalkyl, aminocarbonyl and $C_{1-4}$alkylformamidyl;

cycloalkyl or substituted cycloalkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl; and cycloalkylalkyl or substituted cycloalkylalkyl having one or more substituents independently selected from: amino, amidino, guanidino, hydrazino, $C_{1-4}$alkylamino, $C_{1-4}$dialkylamino, halogen, perfluoro $C_{1-4}$alkyl, $C_{1-4}$alkyl, $C_{1-3}$alkoxy, nitro, carboxy, cyano, sulfuryl and hydroxyl.

In certain embodiment of the compounds described in the preceding paragraph, aryl$C_{1-4}$alkyl is benzyl, bisphenylmethyl, naphthylmethyl or 3,3-bisphenylpropyl; and heterocyclyl$C_{1-4}$alkyl is benzotriazolyl$C_{1-4}$alkyl, benzopyrazolyl$C_{1-4}$alkyl, indazolyl$C_{1-4}$alkyl, isoquinolyl$C_{1-4}$alkyl, benzothiazolyl$C_{1-4}$alkyl, quinolinyl$C_{1-4}$alkyl, thienyl$C_{1-4}$alkyl, tetrahydrofuranyl$C_{1-4}$alkyl, pyridinyl$C_{1-4}$alkyl, benzimidazolyl$C_{1-4}$alkyl, or indolyl$C_{1-4}$alkyl.

In the embodiment where E is $CHR_3$, the reverse turn mimetic compound of this invention has a structure of Formula (II):

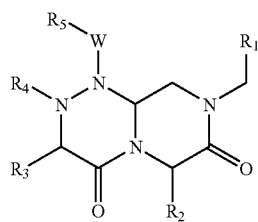

(II)

wherein W is —(C=O)NH—, —(C=O)O—, —(C=O)S—, —S(O)$_2$— or a bond; and each of $R_1$, $R_2$, $R_3$, $R_4$ and $R_5$ is the same or different and independently an amino side chain moiety or an amino acid side chain derivative.

In certain embodiments, $R_1$ of compounds of Formula (II) is benzotriazolyl or substituted benzotriazolyl and it may be benzotriazolyl or substituted benzotriazolyl having one or more substituents independently selected from $C_{1-7}$alkyl, carboxyalkyl, $C_{1-2}$alkyl-heterocyclylcarbonylalkyl, and aminocarbonyl;

$R_2$, $R_4$ and $R_5$ are independently selected from the group consisting of:

$C_{1-12}$alkyl or substituted $C_{1-12}$alkyl having one or more substituents independently selected from: halogen, cyano, $C_{1-6}$alkoxy, amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{2-12}$alkenyl or substituted $C_{2-12}$alkenyl having one or more substituents independently selected from: amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{6-12}$aryl or substituted $C_{6-12}$aryl having one or more substituents independently selected from: halogen, amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{1-6}$alkoxy, $C_{6-13}$heterocyclylalkyl, which has 1 to 2 heteroatoms selected from nitrogen, oxygen or sulfur, or substituted $C_{6-13}$heterocyclylalkyl which has 1 to 2 heteroatoms selected from nitrogen, oxygen or sulfur and has one or more substituents independently selected from: halogen, $C_{1-6}$alkyl, $C_{1-6}$alkoxy, cyano, and hydroxyl; and $C_{7-13}$arylalkyl or substituted $C_{7-13}$arylalkyl having one or more substituents independently selected from: amino, amidino, guanidino, hydrazino, $C_{1-4}$alkylamino, $C_{1-4}$dialkylamino, halogen, perfluoro $C_{1-6}$alkyl, $C_{1-6}$alkoxy, nitro, carboxy, cyano, sulfuryl, hydroxyl, phosphate, dimethylaminoacetate, dimethylaminoalkylcarbamate, and diethylphosphono-acetamido; and $R_3$ is selected from the group consisting of:
hydrogen;
$C_{1-12}$alkyl or substituted $C_{1-12}$alkyl having one or more substituents independently selected from: halogen, cyano, $C_{1-6}$alkoxy, amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{2-12}$alkenyl or substituted $C_{2-12}$alkenyl having one or more substituents independently selected from: amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{6-12}$aryl or substituted $C_{6-12}$aryl having one or more substituents independently selected from: halogen, amino, guanidino, $C_{1-4}$alkylguanidino, di$C_{1-4}$alkylguanidino, amidino, $C_{1-4}$alkylamidino, di$C_{1-4}$alkylamidino, $C_{1-5}$alkylamino, di$C_{1-5}$alkylamino, and hydroxyl;

$C_{1-6}$alkoxy;

$C_{6-13}$heterocyclylalkyl, which has 1 to 2 heteroatoms selected from nitrogen, oxygen or sulfur, or substituted $C_{6-13}$heterocyclylalkyl which has 1 to 2 heteroatoms selected from nitrogen, oxygen or sulfur and has one or more substituents independently selected from: halogen, $C_{1-6}$alkyl, $C_{1-6}$alkoxy, cyano, and hydroxyl; and $C_{7-13}$arylalkyl or substituted $C_{7-13}$arylalkyl having one or more substituents independently selected from: amino, amidino, guanidino, hydrazino, $C_{1-4}$alkylamino, $C_{1-4}$dialkylamino, halogen, perfluoro $C_{1-6}$alkyl, $C_{1-6}$alkoxy, nitro, carboxy, cyano, sulfuryl and hydroxyl.

In certain embodiment of the compounds described in the preceding paragraph, $R_1$ of compounds of Formula (II) is benzotriazolyl or substituted benzotriazolyl having one or more substituents independently selected from methyl, carboxymethyl, morpholinylcarbonylmethyl, methylpiperazinyl-carbonylmethyl, $C_{1-7}$alkylaminocarbonylmethyl, $C_{1-4}$dialkylaminocarbonylmethyl, methoxyethylaminocarbonylethyl, aminocarbonylmethyl, and pyridinylmethylaminocarbonylmethy and specific examples of $R_1$ include, but not limited thereto, 1-methyl-1H-benzotriazolyl, 2-methyl-2H-benzotriazolyl, 1-ethoxycarbonylmethyl-1H-benzotriazolyl, 1-hydroxycarbonylmethyl-1H-benzotriazolyl, 1-morpholinyl-N-carbonylmethyl-1H-benzotriazolyl, 1-N-methylpiperazinyl-N-carbonylmethyl-1H-benzotriazolyl, 1-aminocarbonylmethyl-1H-benzotriazolyl, 1-methyl aminocarbonylmethyl-1H-benzotriazolyl, and 1-pyrdinylmethylaminocarbonylmethyl-1H-benzotriazolyl;

In certain embodiment of the compounds described in the preceding paragraph, $R_2$ and $R_5$ are independently $C_{1-12}$alkyl, $C_{6-12}$aryl, $C_{7-12}$arylalkyl, $C_{6-11}$heterocyclylalkyl, hydroxybenzyl, or substituted benzyl having a substituents selected from phosphate, dimethylaminoacetate, (2-dimethylaminoethyl)-carbamate, and diethyl-phosphono-acetamido;

$R_3$ is hydrogen or $C_{1-12}$alkyl; and
$R_4$ is $C_{1-12}$alkyl, $C_{7-12}$arylalkyl, or $C_{2-12}$alkenyl.

These compounds may be prepared by utilizing appropriate starting component molecules (hereinafter referred to as "component pieces"). Briefly, in the synthesis of reverse-turn mimetic structures having Formula (I), the reverse-turn mimetic structures of Formula (I) may be prepared by sequential coupling of the individual component pieces either stepwise in solution or by solid phase synthesis as commonly practiced in solid phase peptide synthesis, followed by cyclizing to yield the reverse-turn mimetic structures of this invention. Alternatively, first and second component pieces are coupled to form a combined first-second intermediate, if necessary, third and/or fourth component pieces are coupled to form a combined third-fourth intermediate (or, if commercially available, a single third intermediate may be used), the combined first-second intermediate and third-fourth intermediate (or third intermediate) are then coupled to provide a first-second-third-fourth intermediate (or first-second-third intermediate) which is cyclized to yield the reverse-turn mimetic structures of this invention.

Specific component pieces and the assembly thereof to prepare compounds of the present invention are illustrated in FIG. 1. For example, a "first component piece" may have the following formula S1:

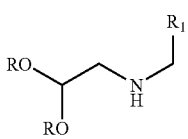
(S1)

wherein $R_1$ is as defined above, and R is a protective group suitable for use in peptide synthesis, where this protection group may be joined to a polymeric support to enable solid-phase synthesis. Suitable R groups include alkyl groups and, in a preferred embodiment, R is a methyl group. In FIG. 1, one of the R groups is a polymeric (solid) support, indicated by "Pol" in the Figure. Such first component pieces may be readily synthesized by reductive amination of $H_2N$—C—$R_1$ with $CH(OR)_2$—CHO, or by a displacement reaction between $H_2N$—C—$R_1$ and $CH(OR)_2$—$CH_2$-LG (wherein LG refers to a leaving group, e.g., a halogen (Hal) group).

A "second component piece" may have the following formula S2:

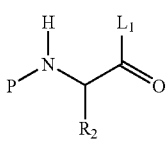
(S2)

where P is an amino protection group suitable for use in peptide synthesis, $L_1$ is hydroxyl or a carboxyl-activation group, and $R_2$ is as defined above. Preferred protection groups include t-butyl dimethylsilyl (TBDMS), t-butyloxycarbonyl (BOC), methyloxycarbonyl (MOC), 9H-fluorenylmethyloxycarbonyl (FMOC), and allyloxycarbonyl (Alloc). N-Protected amino acids are commercially available; for example, FMOC amino acids are available from a variety of sources. In order for the second component piece to be reactive with the first component piece, $L_1$ is a carboxyl-activation group, and the conversion of carboxyl groups to activated carboxyl groups may be readily achieved by methods known in the art for the activation of carboxyl groups. Suitable activated carboxylic acid groups include acid halides where $L_1$ is a halide such as chloride or bromide, acid anhydrides where $L_1$ is an acyl group such as acetyl, reactive esters such as N-hydroxysuccinimide esters and pentafluorophenyl esters, and other activated intermediates such as the active intermediate formed in a coupling reaction using a carbodiimide such as dicyclohexylcarbodiimide (DCC). Accordingly, commercially available N-protected amino acids may be converted to carboxylic activated forms by means known to one of skill in the art.

In the case of the azido derivative of an amino acid serving as the second component piece, such compounds may be prepared from the corresponding amino acid by the reaction disclosed by Zaloom et al. (J. Org. Chem. 46:5173-76, 1981).

A "third component piece" of this invention may have the following formula S3:

(S3)

where $R_4$, E, and $L_1$ are as defined above. Suitable third component pieces are commercially available from a variety of sources or can be prepared by methods well known in organic chemistry.

FIG. 1 illustrates the preparation of compounds of Formula (I).

Thus, as illustrated above, the reverse-turn mimetic compounds of Formula (I) may be synthesized by reacting a first component piece with a second component piece to yield a combined first-second intermediate, followed by reacting the combined first-second intermediate with third component pieces sequentially to provide a combined first-second-third-fourth intermediate, and then cyclizing this intermediate to yield the reverse-turn mimetic structure.

The syntheses of representative component pieces of this invention are described in Preparation Examples.

The reverse-turn mimetic structures of Formulae (I) and (II) may be made by techniques analogous to the modular component synthesis disclosed above, but with appropriate modifications to the component pieces.

The reverse-turn mimetic structures of the present invention are useful as bioactive agents, such as diagnostic, prophylactic, and therapeutic agents. For example, the reverse-turn mimetic structures of the present invention may be used for modulating a cell signaling transcription factor related peptides in a warm-blooded animal, by a method comprising administering to the animal an effective amount of the compound of Formula (I).

Further, the reverse-turn mimetic structures of the present invention may also be effective for inhibiting peptide binding to PTB domains in a warm-blooded animal; for modulating G protein coupled receptor (GPCR) and ion channel in a warm-blooded animal; for modulating cytokines in a warm-blooded animal.

It has been found that the compounds of the Formula (I), especially compounds of Formula (III) are effective for inhibiting or treating disorders modulated by Wnt-signaling pathway, such as cancer.

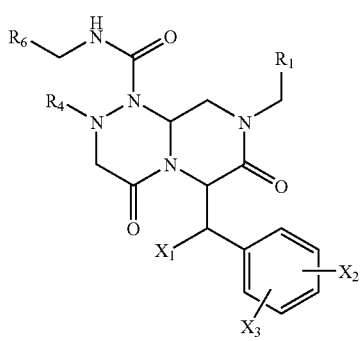

(III)

Formula (III) is shown above, wherein each of $R_1$, $R_4$, and $R_6$ is the same or different and independently an amino acid side chain moiety or an amino acid side chain derivative, $X_1$ may be hydrogen, hydroxyl, or halogen, and $X_2$ and $X_3$ may be independently hydrogen, hydroxyl, or any groups that may make the compound a prodrug, such as phosphate, carboxylate, carbamate and substituted amine.

In certain embodiments of the compounds of Formula (III), $R_1$ is benzotriazolyl or substituted benzotriazolyl having one or more substituents independently selected from $C_{1-7}$alkyl, carboxyalkyl, $C_{1-2}$alkyl-heterocyclylcarbonylalkyl, and aminocarbonyl;

$R_6$ is $C_{6-12}$aryl or substituted $C_{6-12}$aryl having one or more substituents independently selected from the group consisting of: halogen; hydroxyl; cyano; $C_{1-6}$alkyl; and $C_{1-6}$alkoxy; or $C_{5-12}$heterocyclyl or substituted $C_{5-12}$heterocyclyl having one or more substituents independently selected from: halogen, hydroxyl, cyano, $C_{1-6}$alkyl, and $C_{1-6}$alkoxy;

$R_4$ is $C_{1-6}$alkyl, $C_{1-6}$alkoxy, $C_{2-6}$alkenyl or perfluoro$C_{1-6}$ alkyl;

$X_1$ is hydrogen, hydroxyl or halogen; and each of $X_2$ and $X_3$ is independently hydrogen, hydroxyl, phosphate, dimethylaminoacetate, (2-dimethylamino-ethyl)-carbamate, diethyl-phosphono-acetamido or halogen.

In certain embodiment of the compounds described in the preceding paragraph, $R_1$ is selected from the group consisting of benzotriazolyl or substituted benzotriazolyl having one or more substituents independently selected from methyl, carboxymethyl, morpholinylcarbonylmethyl, methylpiperazinyl-carbonylmethyl, $C_{1-7}$alkylaminocarbonylmethyl, $C_{1-4}$dialkylaminocarbonylmethyl, methoxyethylaminocarbonylethyl, aminocarbonylmethyl, and pyridinylmethylaminocarbonylmethyl and specific examples of $R_1$ include, but not limited thereto, 1-methyl-1H-benzotriazolyl, 2-methyl-2H-benzotriazolyl, 1-ethoxycarbonylmethyl-1H-benzotriazolyl, 1-hydroxycarbonylmethyl-1H-benzotriazolyl, 1-morpholinyl-N-carbonylmethyl-1H-benzotriazolyl, 1-N-methylpiperazinyl-N-carbonylmethyl-1H-benzotriazolyl, 1-aminocarbonylmethyl-1H-benzotriazolyl, 1-methylaminocarbonylmethyl-1H-benzotriazolyl, and 1-pyrdinylmethylaminocarbonylmethyl-1H-benzotriazolyl; and $R_4$ is $C_{1-3}$alkyl or allyl; and $R_6$ is phenyl or substituted phenyl having one or more substituents independently selected from: halogen, hydroxyl, cyano, $C_{1-6}$alkyl and $C_{1-6}$alkoxy; or pyridyl or substituted pyridyl having one or more substituents independently selected from: halogen, hydroxyl, cyano, $C_{1-6}$alkyl and $C_{1-6}$alkoxy.

In another aspect of this invention, prodrugs derived from compounds having general Formula (I) are disclosed. The prodrugs generally increase aqueous solubility and thus bioavailability of compounds having general Formula (I). In certain embodiments, the prodrugs of the present invention have the following general Formula (IV):

(III)-$R_7$  (IV)

wherein one of $R_1$, $R_4$, $R_6$, $X_1$, $X_2$, and $X_3$ is linked to $R_7$ via Y, wherein:

Y is an oxygen, sulfur, or nitrogen in $R_1$, $R_4$, or $R_6$, or an oxygen in $X_1$, $X_2$, or $X_3$; and $R_7$ is hydroxyalkyl, glycosyl, phosphoryloxymethyloxycarbonyl, substituted or unsubstituted piperidine carbonyloxy, or a salt thereof; or Y—$R_7$ is an amino acid residue, a combination of amino acid residues, phosphate, hemimalate, hemisuccinate, dimethylaminoalkylcarbamate, dimethylaminoacetate, or a salt thereof; and when not linked to $R_7$; $R_1$, $R_4$, $R_6$, $X_1$, $X_2$, and $X_3$ are defined as they are in Formula (III).

In another aspect of this invention, libraries containing reverse-turn mimetic structures of the present invention are disclosed. Once assembled, the libraries of the present invention may be screened to identify individual members having bioactivity. Such screening of the libraries for bioactive members may involve; for example, evaluating the binding activity of the members of the library or evaluating the effect the library members have on a functional assay. Screening is normally accomplished by contacting the library members (or a subset of library members) with a target of interest, such as, for example, an antibody, an enzyme, a receptor or a cell line. Library members which are capable of interacting with the target of interest are referred to herein as "bioactive library members" or "bioactive mimetics". For example, a bioactive mimetic may be a library member which is capable of binding to an antibody or receptor, or which is capable of inhibiting an enzyme, or which is capable of eliciting or antagonizing a functional response associated, for example, with a cell line. In other words, the screening of the libraries of the present invention determines which library members are capable of interacting with one or more biological targets of interest. Furthermore, when interaction does occur, the bioactive mimetic (or mimetics) may then be identified from the library members. The identification of a single (or limited number) of bioactive mimetic(s) from the library yields reverse-turn mimetic structures which are themselves biologically active, and thus are useful as diagnostic, prophylactic or therapeutic agents, and may further be used to significantly advance identification of lead compounds in these fields.

Synthesis of the peptide mimetics of the library of the present invention may be accomplished using known peptide synthesis techniques, in combination with the first, second and third component pieces of this invention. More specifically, any amino acid sequence may be added to the N-terminal and/or C-terminal of the conformationally constrained reverse-turn mimetic. To this end, the mimetics may be synthesized on a solid support (such as PAM resin) by known techniques (see, e.g., John M. Stewart and Janis D. Young, Solid Phase Peptide Synthesis, 1984, Pierce Chemical Comp., Rockford, Ill.) or on a silyl-linked resin by alcohol attachment (see Randolph et al., *J. Am. Chem. Soc.* 117:5712-14, 1995).

In addition, a combination of both solution and solid phase synthesis techniques may be utilized to synthesize the peptide mimetics of this invention. For example, a solid support may be utilized to synthesize the linear peptide sequence up to the point that the conformationally constrained reverse-turn is added to the sequence. A suitable conformationally constrained reverse-turn mimetic structure which has been previously synthesized by solution synthesis techniques may then be added as the next "amino acid" to the solid phase synthesis (i.e., the conformationally constrained reverse-turn mimetic, which has both an N-terminus and a C-terminus, may be utilized as the next amino acid to be added to the linear peptide). Upon incorporation of the conformationally constrained reverse-turn mimetic structures into the sequence, additional amino acids may then be added to complete the peptide bound to the solid support. Alternatively, the linear N-terminus and C-terminus protected peptide sequences may be synthesized on a solid support, removed from the support, and then coupled to the conformationally constrained reverse-turn mimetic structures in solution using known solution coupling techniques.

In one aspect of this invention, methods for constructing the libraries are disclosed. Traditional combinatorial chemistry techniques (see, e.g., Gallop et al., *J. Med. Chem.* 37:1233-1251, 1994) permit a vast number of compounds to be rapidly prepared by the sequential combination of reagents to a basic molecular scaffold. Combinatorial techniques have been used to construct peptide libraries derived from the naturally occurring amino acids. For example, by taking 20 mixtures of 20 suitably protected and different amino acids and coupling each with one of the 20 amino acids, a library of 400 (i.e., $20^2$) dipeptides is created. Repeating the procedure seven times results in the preparation of a peptide library comprised of about 26 billion (i.e., $20^8$) octapeptides.

Specifically, synthesis of the peptide mimetics of the library of the present invention may be accomplished using known peptide synthesis techniques, for example, the General Scheme of Reverse-Turn Mimetic Library, as follows:

the above scheme Pe represents a bromoacetal resin (Advanced ChemTech) and detailed procedure is illustrated below.

Step 1

A bromoacetal resin (37 mg, 0.98 mmol/g) and a solution of $R_1$-amine in DMSO (1.4 mL) were placed in a Robbins block (FlexChem) having 96 well plates. The reaction mixture was shaken at 60° C. using a rotating oven [Robbins Scientific] for 12 hours. The resin was washed with DMF, MeOH, and then DCM Step 2

A solution of commercially available Fmoc-NH—CH($R_2$)—COOH (4 equiv.), PyBob (4 equiv.), HOAt (4 equiv.), and DIEA (12 equiv.) in DMF was added to the resin. After the reaction mixture was shaken for 12 hours at room temperature, the resin was washed with DMF, MeOH, and then DCM.

Step 3

To the resin swollen by DMF before reaction was added 25% piperidine in DMF and the reaction mixture was shaken for 30 min at room temperature. This deprotection step was repeated again and the resin was washed with DMF, Methanol, and then DCM. A solution of hydrazine acid (4 equiv.), HOBt (4 equiv.), and DIC (4 equiv.) in DMF was added to the resin and the reaction mixture was shaken for 12 hours at room temperature. The resin was washed with DMF, MeOH, and then DCM.

Step 4

The resin obtained in Step 3 was treated with formic acid (1.2 mL each well) for 18 hours at room temperature. After the resin was removed by filtration, the filtrate was condensed

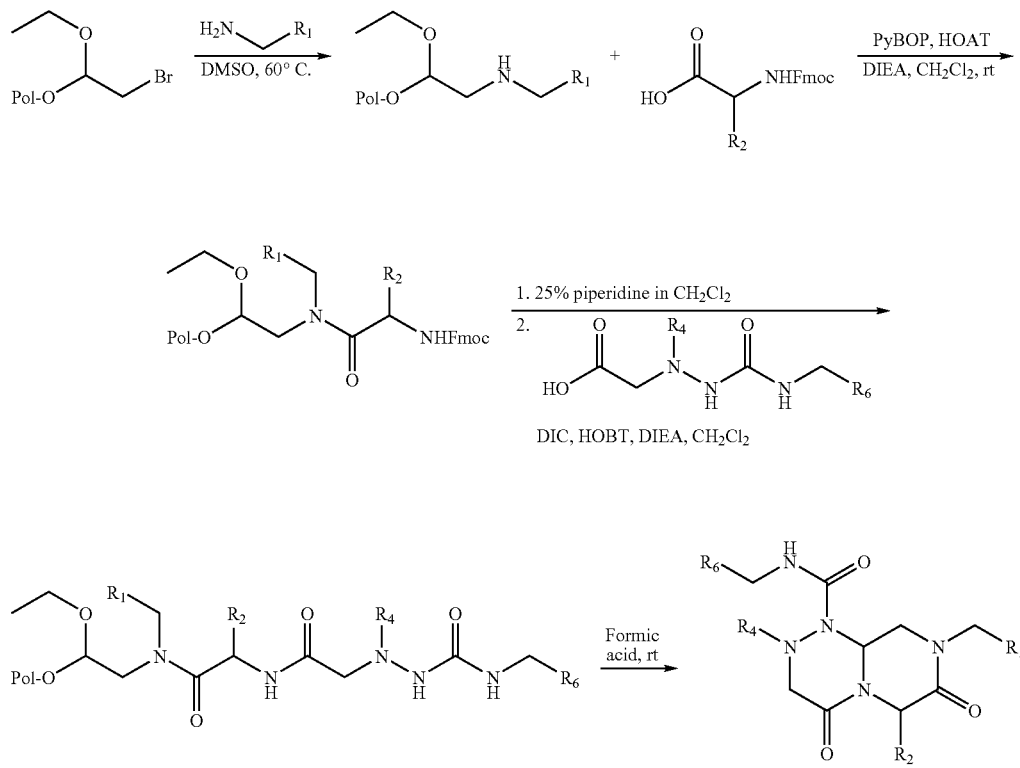

Synthesis of the peptide mimetics of the libraries of the present invention was accomplished using a FlexChem Reactor Block which has 96 well plates by known techniques. In under a reduced pressure using SpeedVac [SAVANT] to give the product as oil. The product was diluted with 50% water/acetonitrile and then lyophilized after freezing.

To generate these block libraries the key intermediate hydrazine acids were synthesized according to the procedure illustrated in Preparation Example 1.

Table 2 shows the compounds which were prepared according to the present invention of which representative preparation is given in Preparation Examples.

TABLE 2

| | REVERSE TURN MIMETICS LIBRARY | | |
|---|---|---|---|
| NO | Structure | M.W. Formula | M + H |
| 1 | 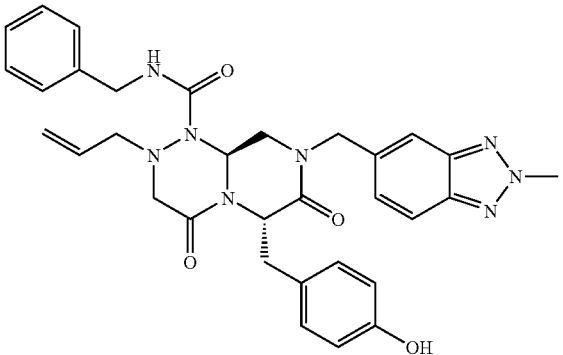 | 594.66 C32H34N8O4 | 595 |
| 2 | 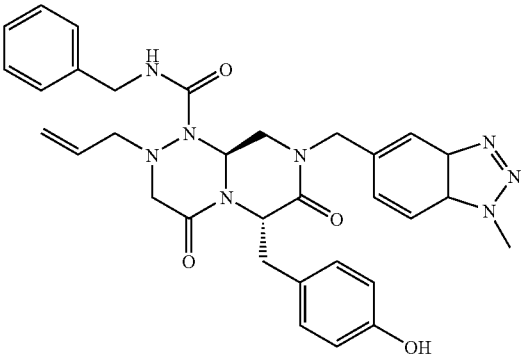 | 594.66 C32H34N8O4 | 595 |
| 3 | 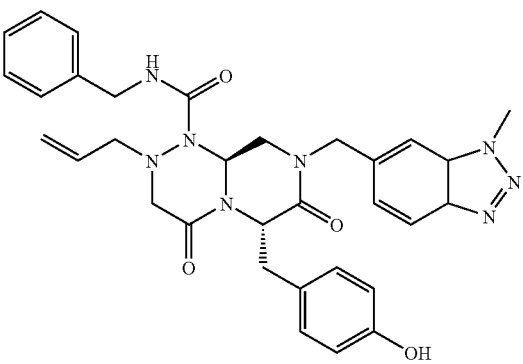 | 594.66 C32H34N8O4 | 595 |

TABLE 2-continued
REVERSE TURN MIMETICS LIBRARY
| NO | Structure | M.W. Formula | M + H |
|---|---|---|---|
| 4 | 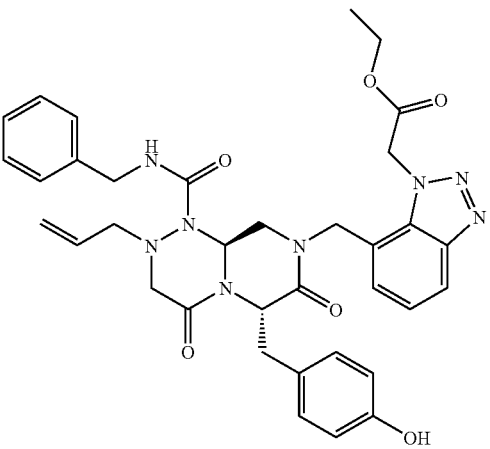 | 666.73 C35H38N8O6 | 668 |
| 5 | 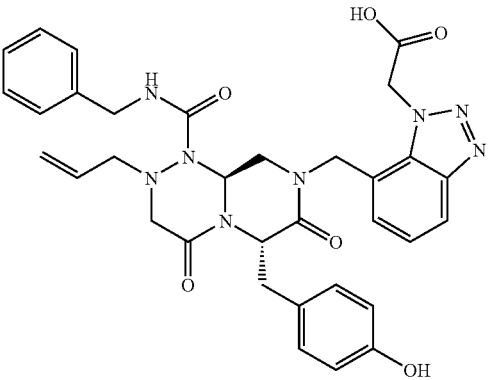 | 638.67 C33H34N8O6 | 640 |
| 6 | 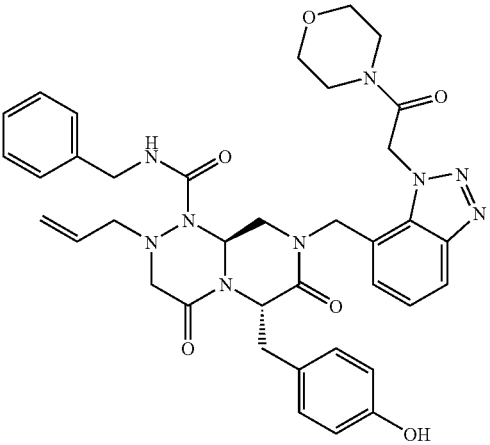 | 707.78 C37H41N9O6 | 709 |

TABLE 2-continued

REVERSE TURN MIMETICS LIBRARY

| NO | Structure | M.W. Formula | M + H |
|----|-----------|--------------|-------|
| 7  | 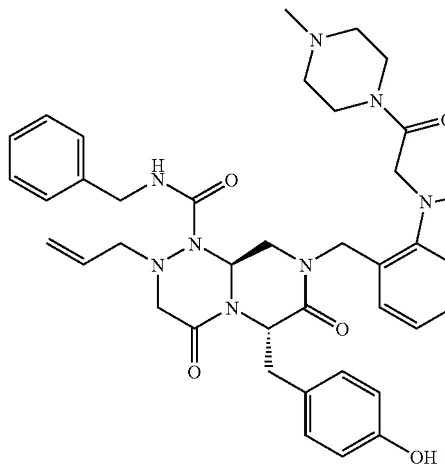          | 720.82 C38H44N10O5 | 722 |
| 8  | 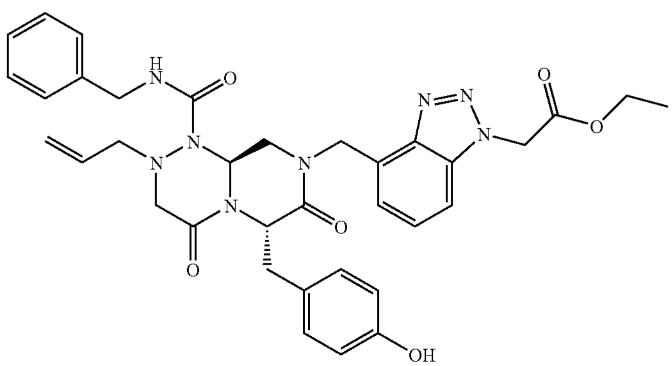          | 666.73 C35H38N8O6 | 668 |
| 9  | 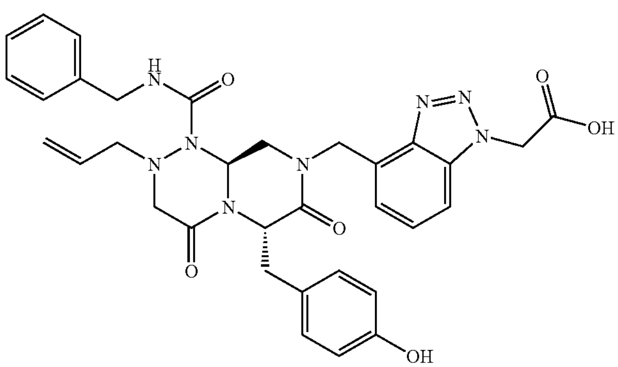          | 638.67 C33H34N8O6 | 640 |
| 10 | 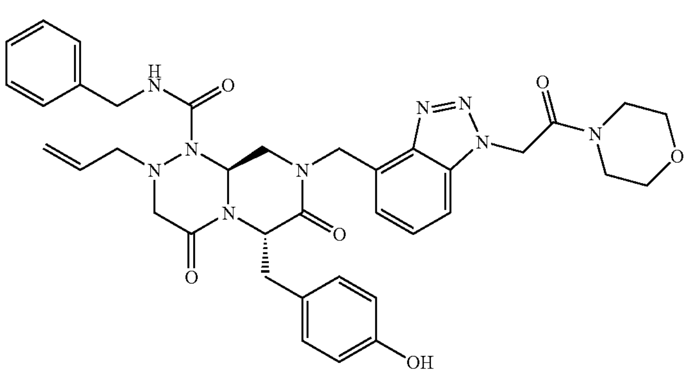          | 707.78 C37H41N9O6 | 709 |

TABLE 2-continued

REVERSE TURN MIMETICS LIBRARY

| NO | Structure | M.W. Formula | M + H |
|---|---|---|---|
| 11 | 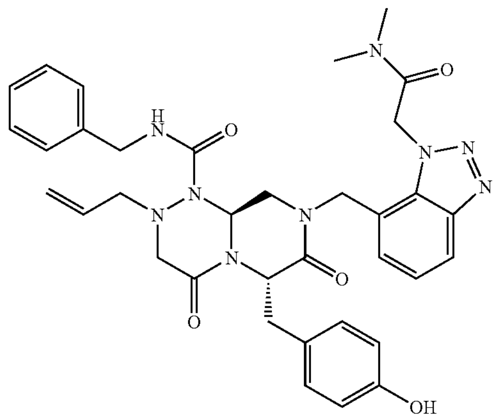 | 665.74 C35H39N9O5 | 667 |
| 12 | 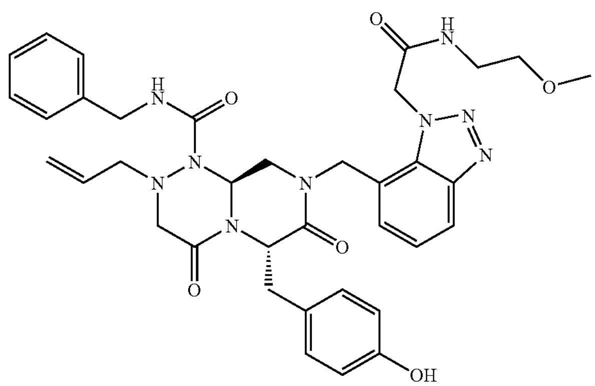 | 695.77 C36H41N9O6 | 697 |
| 13 | 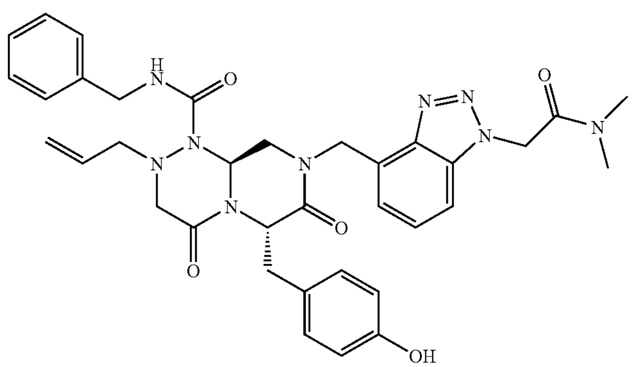 | 665.74 C35H39N9O5 | 667 |
| 14 | 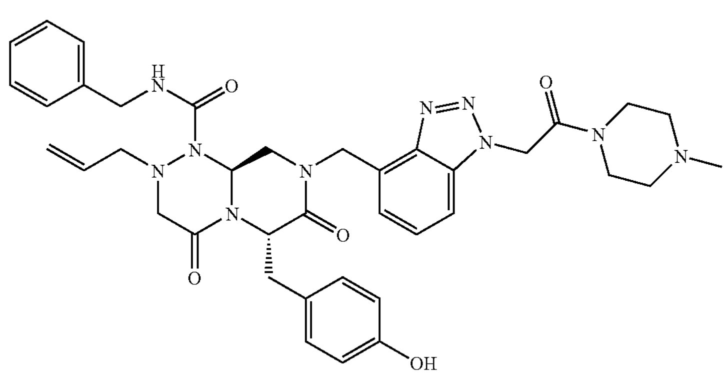 | 622.67 C33H34N8O5 | 624 |

TABLE 2-continued

REVERSE TURN MIMETICS LIBRARY

| NO | Structure | M.W. Formula | M + H |
|---|---|---|---|
| 15 | 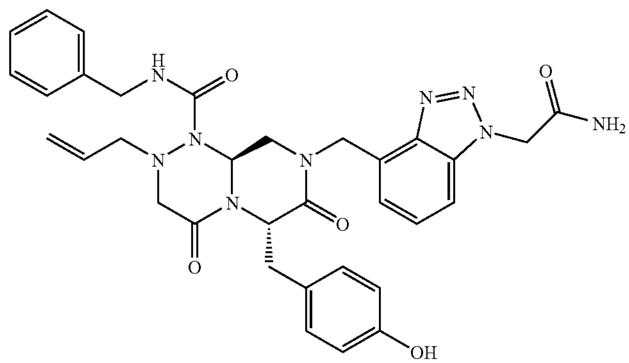 | 720.82 C38H44N10O5 | 722 |
| 16 | 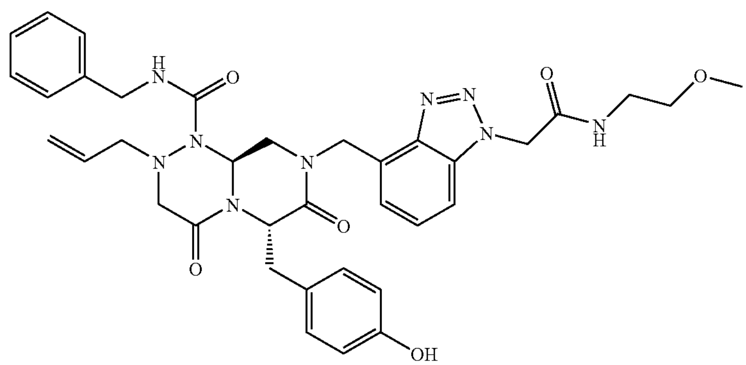 | 637.69 C33H35N9O5 | 639 |
| 17 | 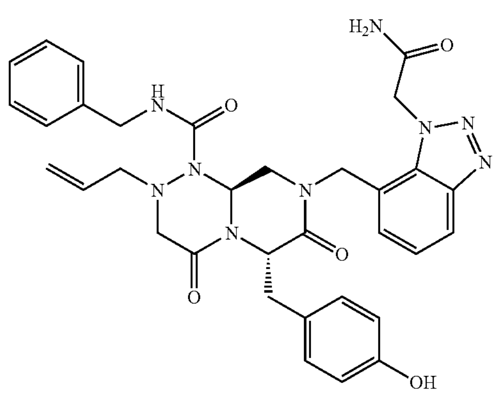 | 695.77 C36H41N9O6 | 697 |
| 18 | 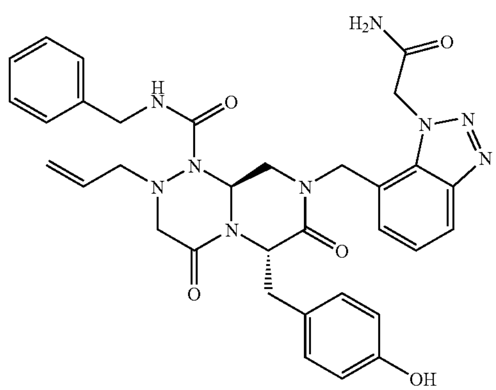 | 637.69 C33H35N9O5 | 639 |

TABLE 2-continued

REVERSE TURN MIMETICS LIBRARY

| NO | Structure | M.W. Formula | M + H |
|----|-----------|--------------|-------|
| 19 | 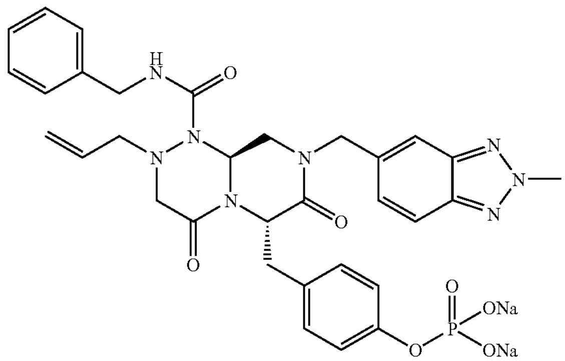 | 718.61 C32H33N8Na2O7P | 720 |
| 20 | 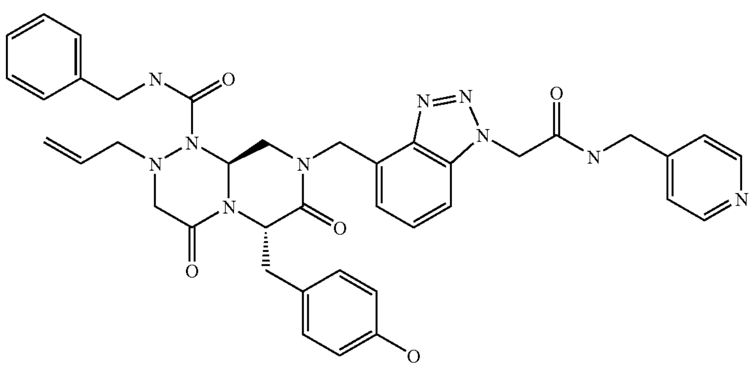 | 728.81 C39H40N10O5 | 730 |
| 21 | 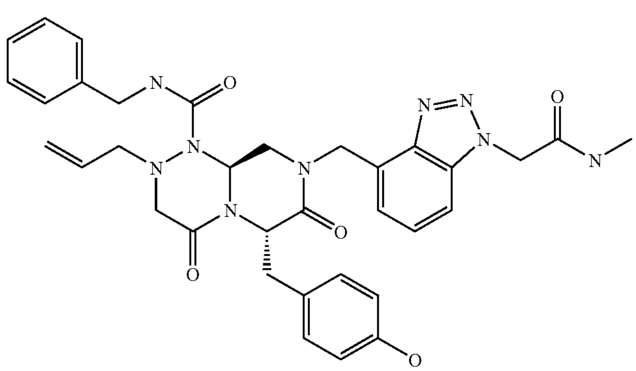 | 651.72 C34H37N9O5 | 653 |

Below are NMR data of some of the compounds prepared according to the above procedure:

2-allyl-6-(4-hydroxy-benzyl)-8-(2-methyl-2H-benzo-triazol-5-ylmethyl)-4,7-dioxo-hexahydro-pyrazino[2,1-c][1,2,4]triazine-1-carboxylic acid benzylamide

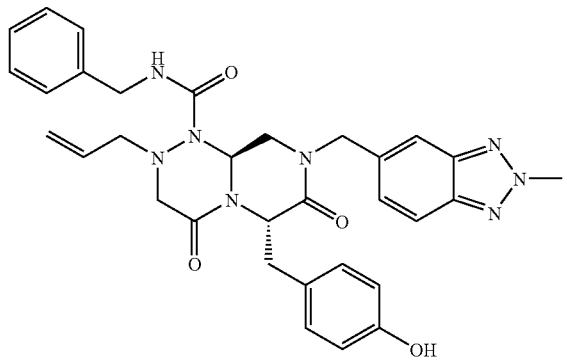

$^1$H NMR (CDCl$_3$): δ 7.849~7.819 (d, J=8.8 Hz, 1H), 7.629 (s, 1H), 7.376~7.209 (m, 5H), 7.003~6.975 (d, J=8.4 Hz, 2H), 6.712~6.670 (t, J=6.0 Hz, 1H), 6.682~6.654 (d, J=8.4 Hz, 2H), 5.698~5.589 (td, J=17.0 Hz, J=10.3 Hz, 1H), 5.438~5.389 (dd, J=10.6 Hz, J=4.0 Hz, 1H), 5.364~5.078 (t, J=5.5 Hz, 1H), 5.112~5.078 (d, J=10.4 Hz, 1H), 4.987~4.927 (d, J=18.0 Hz, 1H), 4.919~4.869 (d, J=14.8 Hz, 1H), 4.682~4.633 (d, J=14.8 Hz, 1H), 4.497 (s, 3H), 4.438=4.270 (qd, J=15.0 Hz, J=6.1 Hz, 2H), 3.479~3.261 (m, 7H)

2-allyl-6-(4-hydroxy-benzyl)-8-(3-methyl-3H-benzo-triazol-5-ylmethyl)-4,7-dioxo-hexahydro-pyrazino[2,1-c][1,2,4]triazine-1-carboxylic acid benzylamide

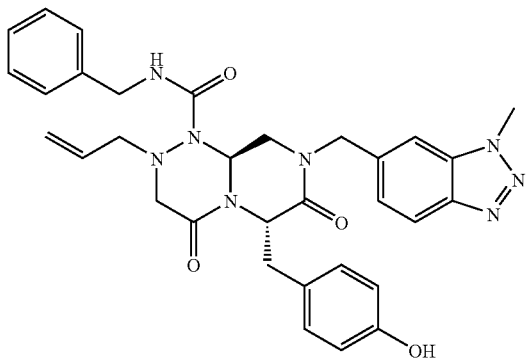

$^1$H NMR (CDCl$_3$): δ 8.006~7.978 (d, J=8.4 Hz, 1H), 7.394~7.221 (m, 7H), 6.951~6.923 (d, J=8.5 Hz, 2H), 6.758~6.718 (t, J=6.2 Hz, 1H), 6.609~6.581 (d, J=8.5 Hz, 2H), 5.689~5.555 (td, J=16.7 Hz, J=6.4 Hz, 1H), 5.386~5.294 (m, 2H), 5.152~5.118 (d, J=10.2 Hz, 1H), 5.042~4.988 (d, J=16.2 Hz, 1H), 4.802 (s, 3H), 4.445~4.266 (m, 6H), 3.531~3.315 (m, 8H), 2-allyl-6-(4-hydroxy-benzyl)-8-(1-methyl-1H-benzo-triazol-5-ylmethyl)-4,7-dioxo-hexahydro-pyrazino[2,1-c][1,2,4]triazine-1-carboxylic acid benzylamide

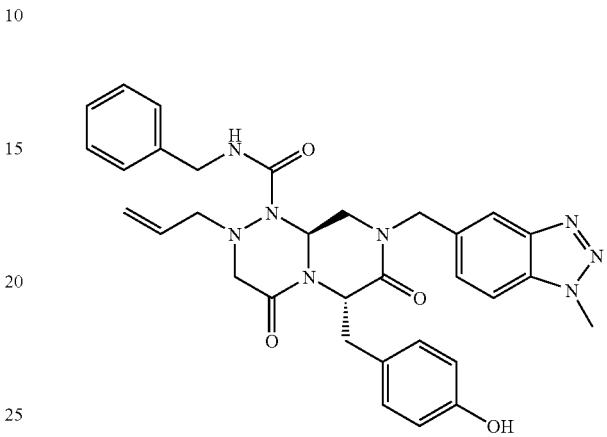

$^1$H NMR (CDCl$_3$): δ 7.736 (s, 1H), 7.529~7.500 (d, J=8.7 Hz, 1H), 7.404~7.211 (m, 6H), 7.011~6.983 (d, J=8.4 Hz, 2H), 6.748~6.720 (d, J=8.4 Hz, 2H), 6.675~6.635 (t, J=6.0 Hz, 1H), 5.680~5.547 (td, J=16.6 Hz, J=6.2 Hz, 1H), 5.680~5.547 (m, 2H), 5.337~4.961 (m, 5H), 4.607~4.558 (d, J=14.8 Hz, 1H), 4.428~4.245 (m, 2H), 4.295 (s, 3H), 3.514~3.223 (m, 9H).

The libraries of the present invention were screened for bioactivity by various techniques and methods. In general, the screening assay may be performed by (1) contacting the mimetics of a library with a biological target of interest, such as a receptor, to allow binding between the mimetics of the library and the target to occur, and (2) detecting the binding event by an appropriate assay, such as the calorimetric assay disclosed by Lam et al. (Nature 354:82-84, 1991) or Griminski et al. (Biotechnology 12:1008-1011, 1994) (both of which are incorporated herein by reference). In a preferred embodiment, the library members are in solution and the target is immobilized on a solid phase. Alternatively, the library may be immobilized on a solid phase and may be probed by contacting it with the target in solution.

Inhibition activity against Wnt signaling was measured by the TopFlash reporter. The lower IC50 value means the higher inhibition activity. A compound can be classified as active if IC50 is 10 μM or below. When IC50 is 5~10 μM, the compound can be a candidate for a pharmaceutical. A compound is deemed strong if IC50 is 1~5 μM, and a compound is deemed very strong if IC50 is 1 μM or below.

Most of the compounds of the present invention showed IC50 of 5 μM or below, that means they have strong inhibition activity against Wnt signaling.

Table 3 below shows compounds for bioactivity test selected from the library of the present invention and IC50 values thereof, which were measured by the Reporter gene assay as described in Example 2.

TABLE 3

IC50(μM) MEASURED BY THE TopFlash REPORTER GENE ASSAY OF SELECTED LIBRARY COMPOUNDS

| NO | Structure | M.W. Formula | RGA, IC50 (μM) TopF |
|---|---|---|---|
| 1 | 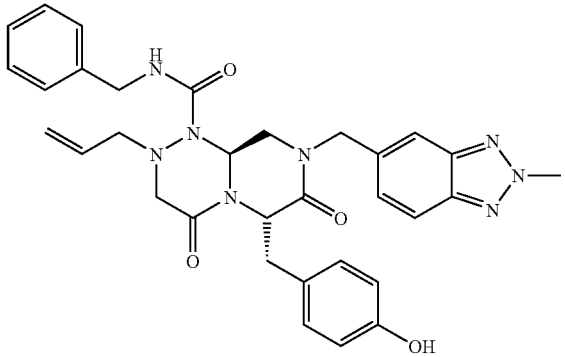 | 594.66 C32H34N8O4 | 1.00 ± 0.25 |
| 2 | 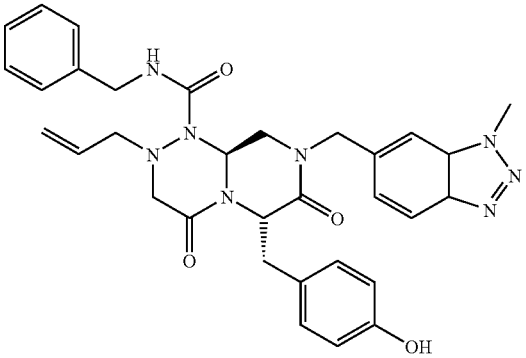 | 594.66 C32H34N8O4 | 3.73 ± 0.67 |

It has been found according to the present invention that compounds of general Formula (I) have less CYP3A4 inhibitory activity (higher IC50). The details of the measurement of CYP3A4 inhibitory activity are disclosed in Example 1. Less CYP3A4 inhibitory activity means that the compounds of the present invention are more pharmacologically favorable in terms of adverse reactions.

Table 4 below shows compounds for bioactivity test selected from the library of the present invention and IC50 values thereof, which were measured by the P450 CYP3A4 Inhibitory Activity Screening as described in Example 1.

TABLE 4

IC50(μM) MEASURED BY P450 CYP3A4 INHIBITORY ACTIVITY SCREENING OF SELECTED LIBRARY COMPOUNDS

| NO | Structure | M.W. Formula | CYP3A4 inhibition, IC50 (μM) fluorescent assay |
|---|---|---|---|
| 1 | 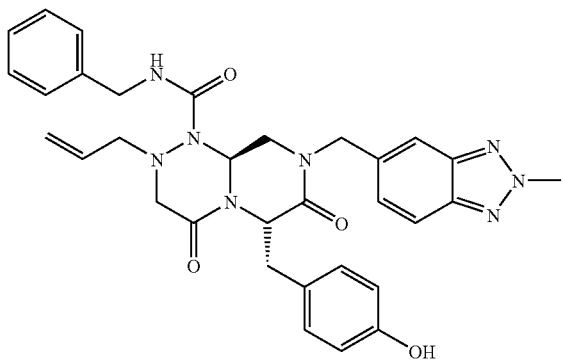 | 594.66 C32H34N8O4 | 19.2 |

TABLE 4-continued

IC50(μM) MEASURED BY P450 CYP3A4 INHIBITORY ACTIVITY SCREENING OF
SELECTED LIBRARY COMPOUNDS

| NO | Structure | M.W. Formula | CYP3A4 inhibition, IC50 (μM) fluorescent assay |
|----|-----------|--------------|-----------------------------------------------|
| 2  | 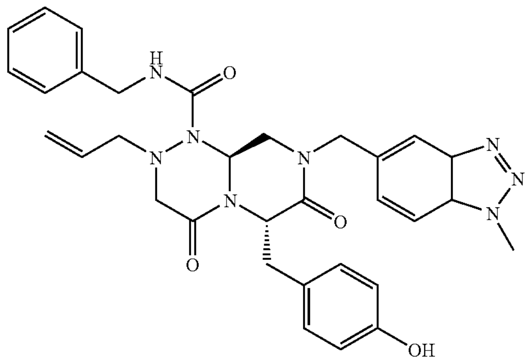          | 594.66 C32H34N8O4 | 18.8 |
| 3  | 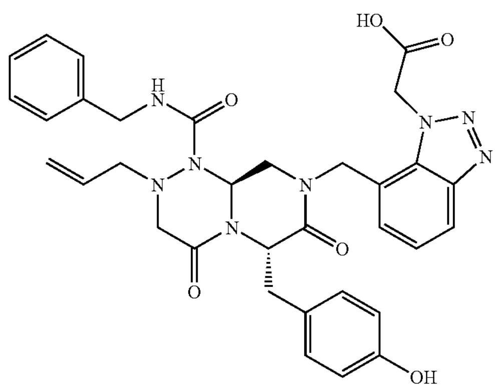          | 638.67 C33H34N8O6 | >50 |
| 4  | 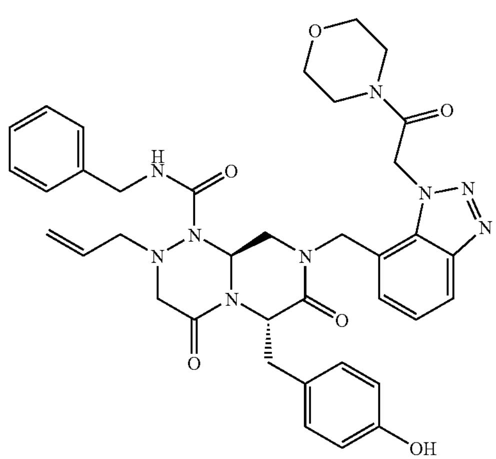          | 707.78 C37H41N9O6 | 6.23 |

TABLE 4-continued

IC50(μM) MEASURED BY P450 CYP3A4 INHIBITORY ACTIVITY SCREENING OF SELECTED LIBRARY COMPOUNDS

| NO | Structure | M.W. Formula | CYP3A4 inhibition, IC50 (μM) fluorescent assay |
|---|---|---|---|
| 5 | 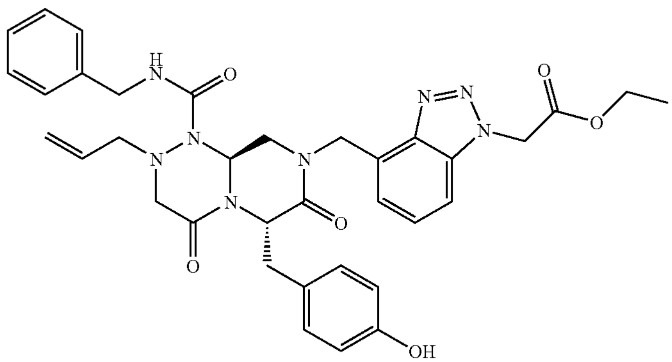 | 666.73 C35H38N8O6 | 7.40 |
| 6 | 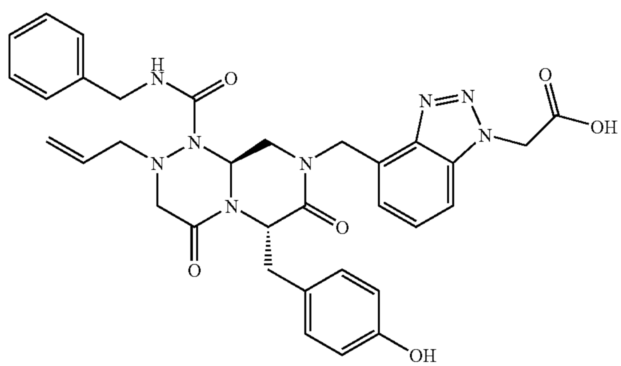 | 638.67 C33H34N8O6 | >50 |
| 7 | 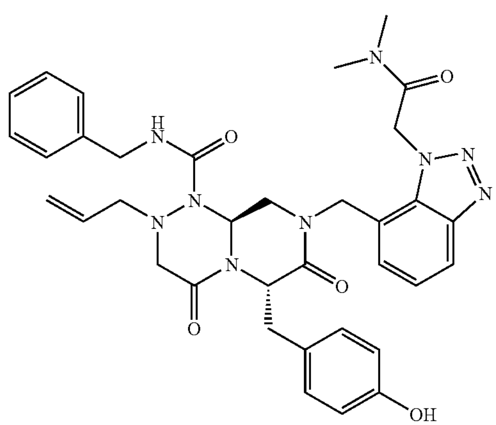 | 665.74 C35H39N9O5 | 41.10 |
| 8 | 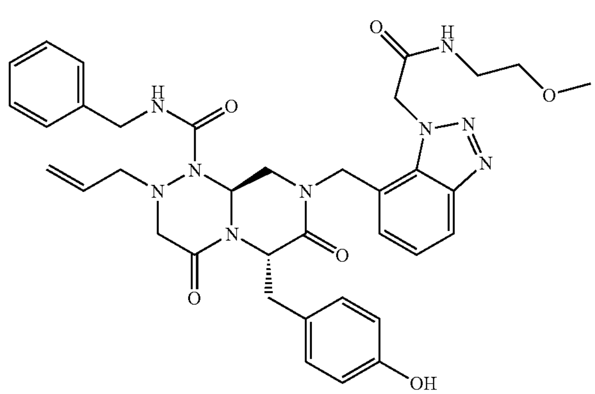 | 695.77 C36H41N9O6 | 46.90 |

TABLE 4-continued

IC50(μM) MEASURED BY P450 CYP3A4 INHIBITORY ACTIVITY SCREENING OF SELECTED LIBRARY COMPOUNDS

| NO | Structure | M.W. Formula | CYP3A4 inhibition, IC50 (μM) fluorescent assay |
|---|---|---|---|
| 9 | 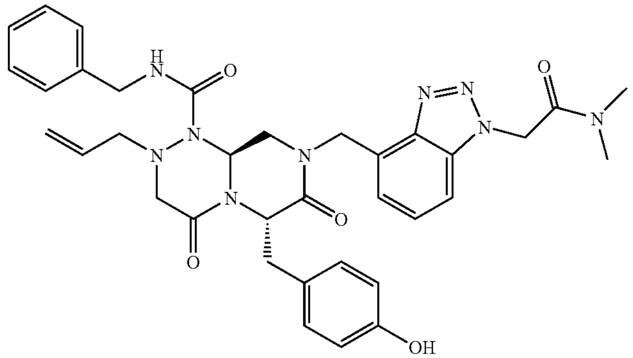 | 665.74 C35H39N9O5 | 38.00 |
| 10 | 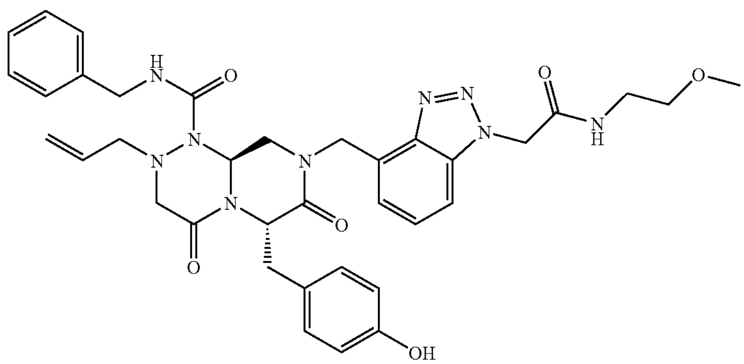 | 637.69 C33H35N9O5 | 12.20 |
| 11 | 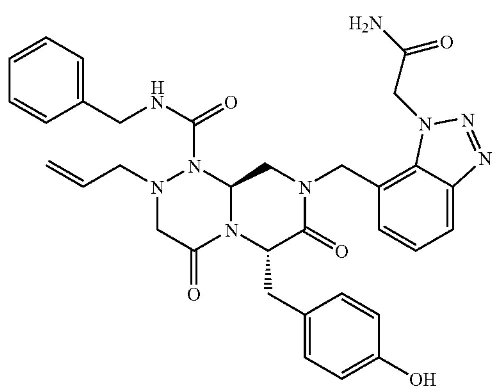 | 695.77 C36H41N9O6 | 37.80 |
| 12 | 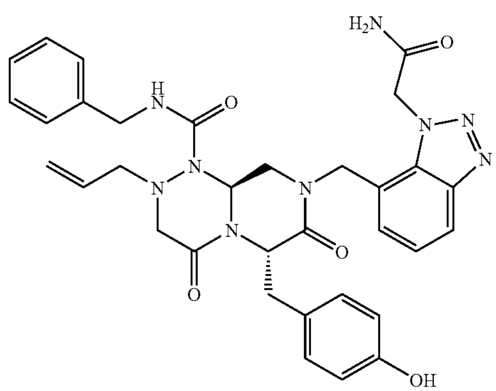 | 637.69 C33H35N9O5 | 33.20 |

TABLE 4-continued

IC50(μM) MEASURED BY P450 CYP3A4 INHIBITORY ACTIVITY SCREENING OF SELECTED LIBRARY COMPOUNDS

| NO | Structure | M.W. Formula | CYP3A4 inhibition, IC50 (μM) fluorescent assay |
|---|---|---|---|
| 13 | 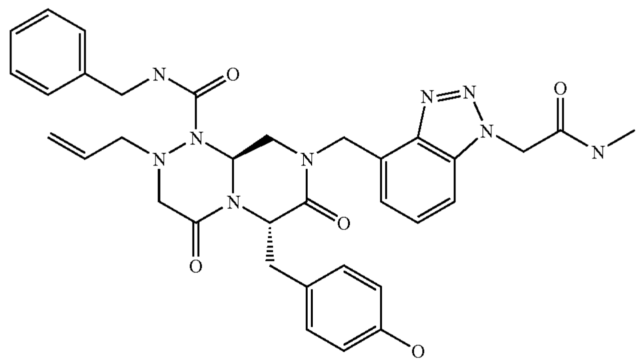 | 651.72 C34H37N9O5 | 32.40 |

The present invention is also related to methods for preventing or treating an acute myeloid leukemia comprising administering to the subject the compound having Formula (I) above.

In one aspect, the present invention provides compounds that inhibit the formation of a complex of β-catenin, p300 and TCF binding onto c-Myc protein and formation of a complex of β-catenin, p300 and TCF binding onto survivin promoter.

In another aspect, the present invention provides compounds, in particular those having Formula (II), that control c-Myc protein.

It has been found according to the present invention that compounds of general Formula (I) affect the cell proliferation and inhibit the growth of AML cancer cells, as described in Example 3.

GI50 of MV-4-11 shows cell growth inhibition activity against AML cancer cells. The lower GI 50 value means the higher inhibition activity. A compound can be classified as active if GI50 is 10 μM or below. When GI50 is 5~10 μM, the compound can be a candidate for a pharmaceutical. A compound is deemed strong if GI50 is 1~5 μM, and a compound is deemed very strong if GI50 is 1 μM or below.

Most of the compounds of the present invention showed GI50 of 5 μM or below, that means they have strong inhibition activity against AML cancer cells.

Table 5 below shows compounds for bioactivity test selected from the library of the present invention and GI50 values thereof, which were measured by Cell Growth Inhibition Assay) as described in Example 3.

TABLE 5

CELL GROWTH INHIBITION ACTIVITY (GI50) ON AML CANCER CELLS OF SELECTED LIBRARY COMPOUNDS

| NO | Structure | MV-4-11, GI50 (μM) |
|---|---|---|
| 1 | 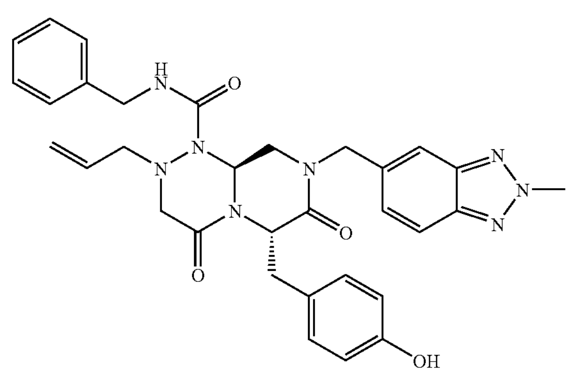 | 0.26 |

TABLE 5-continued

CELL GROWTH INHIBITION ACTIVITY (GI50) ON AML CANCER CELLS OF SELECTED LIBRARY COMPOUNDS

| NO | Structure | MV-4-11, GI50 (μM) |
|----|-----------|---------------------|
| 2 | 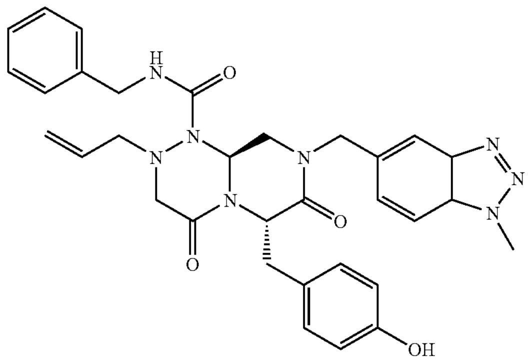 | 1.45 |
| 3 | 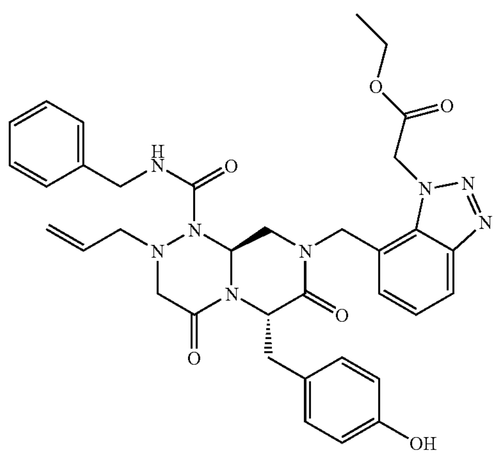 | 0.71 |
| 4 | 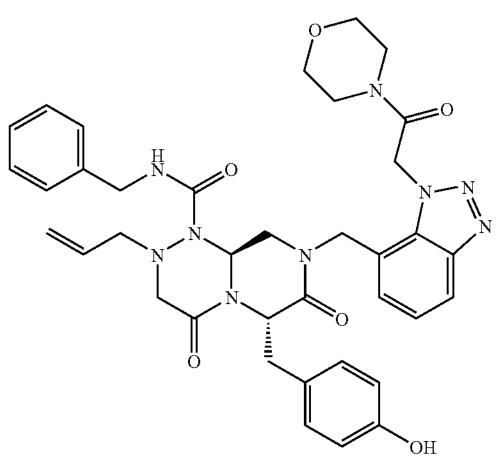 | 0.93 |

TABLE 5-continued

CELL GROWTH INHIBITION ACTIVITY (GI50) ON AML CANCER CELLS OF SELECTED LIBRARY COMPOUNDS

| NO | Structure | MV-4-11, GI50 (µM) |
| --- | --- | --- |
| 5 | 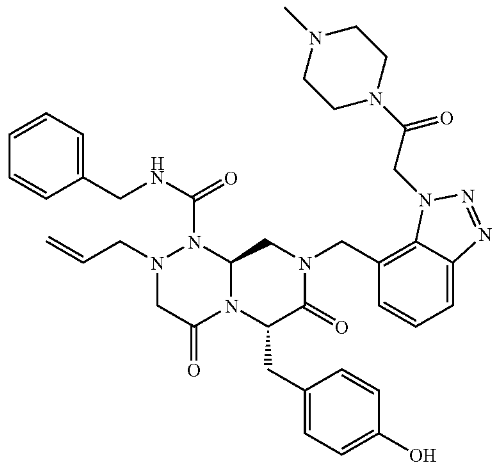 | 2.97 |
| 6 | 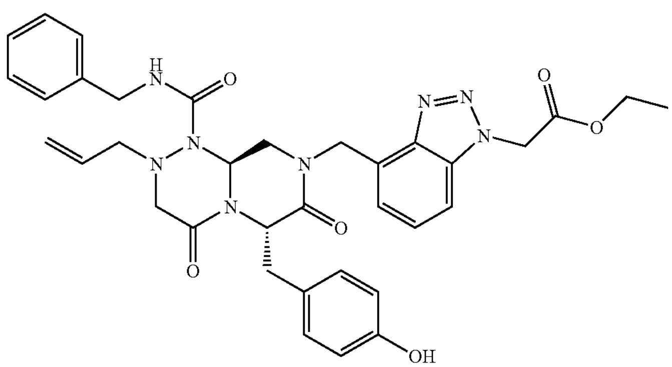 | 0.65 |
| 7 | 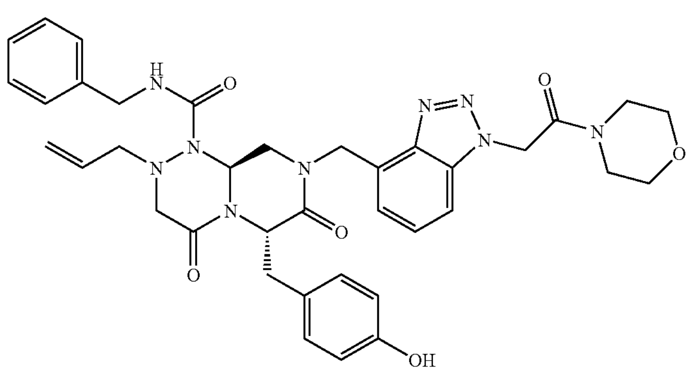 | 0.37 |

TABLE 5-continued
CELL GROWTH INHIBITION ACTIVITY (GI50) ON AML CANCER CELLS OF SELECTED LIBRARY COMPOUNDS
| NO | Structure | MV-4-11, GI50 (µM) |
|---|---|---|
| 8 | 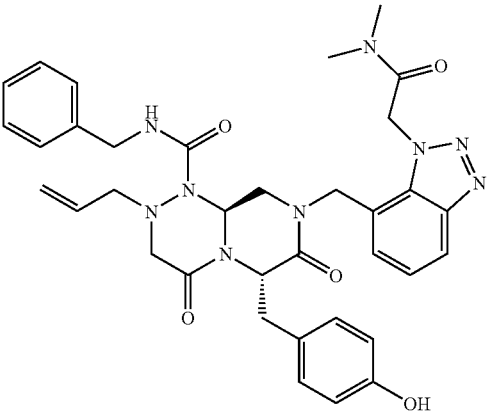 | 1.92 |
| 9 | 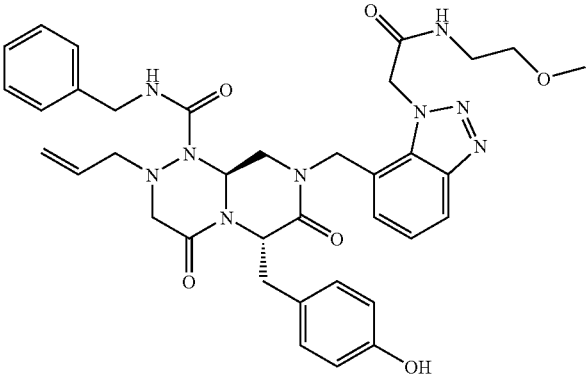 | 1.85 |
| 10 | 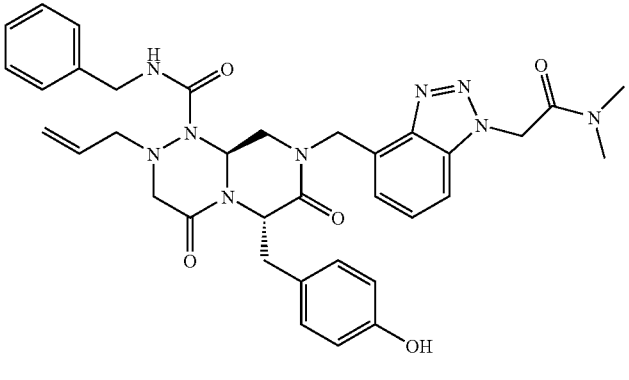 | 0.5 |
| 11 | 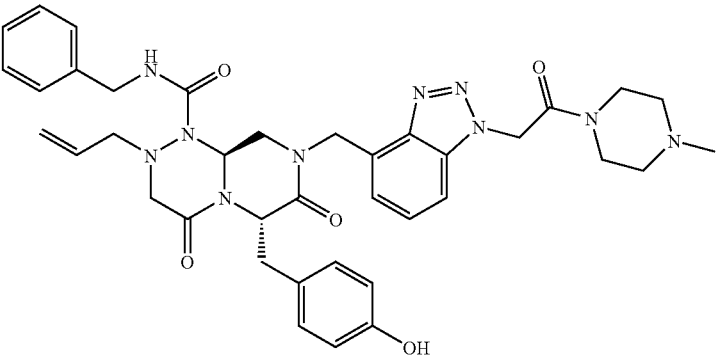 | 0.19 |

TABLE 5-continued

CELL GROWTH INHIBITION ACTIVITY (GI50) ON AML CANCER CELLS OF SELECTED LIBRARY COMPOUNDS

| NO | Structure | MV-4-11, GI50 (μM) |
|---|---|---|
| 12 | 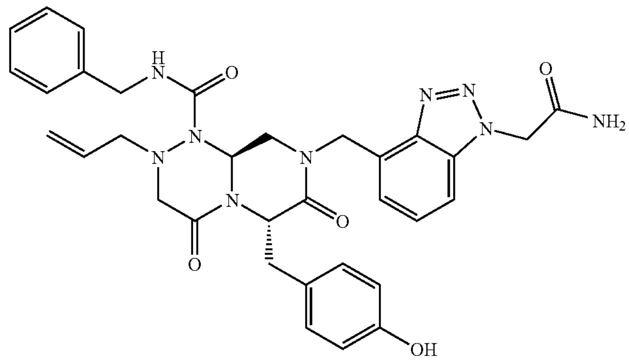 | 0.56 |
| 13 | 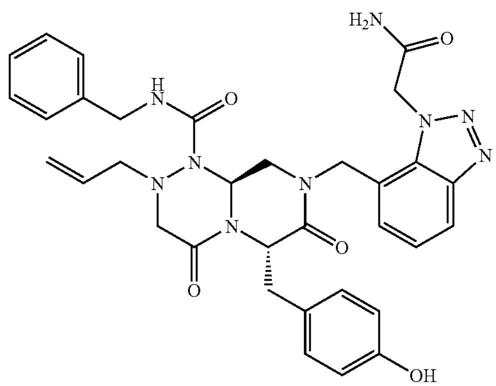 | 3.27 |
| 14 | 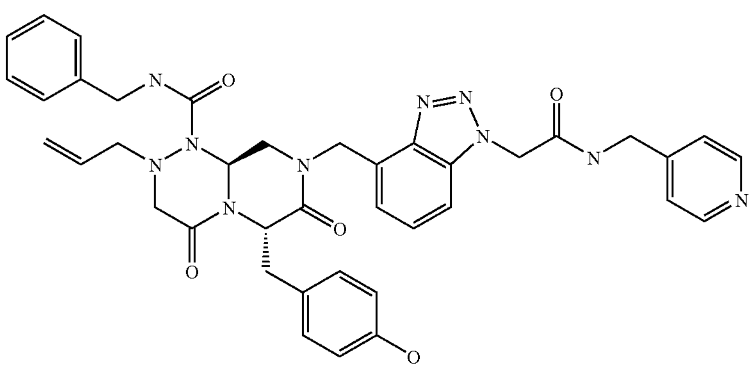 | 0.6 |
| 15 | 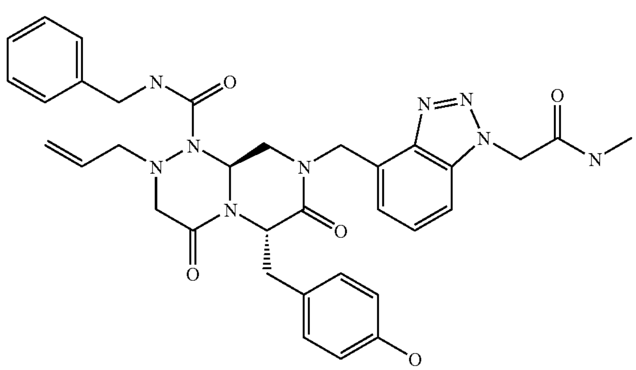 | 0.18 |

The following non-limiting examples illustrate the compounds, and the use of this invention.

Preparation Example 1

Preparation of (N-Fmoc-N'—R$_4$-hydrazino)-acetic acid

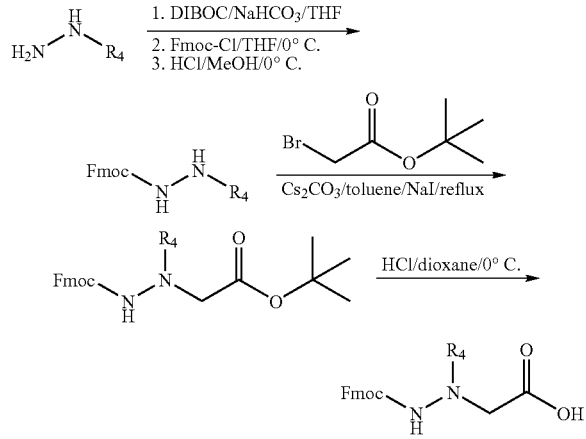

(1) Preparation of N-Fmoc-N'-Methyl Hydrazine

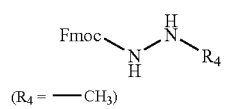

($R_4 = $ —CH$_3$)

A 2 L, two-necked, round-bottomed-flask was fitted with a glass stopper and a calcium tube. A solution of R$_4$-hydrazine (20 g, 139 mmol, where R$_4$ is methyl) in THF (300 mL) was added and a solution of DiBoc (33 g, 153 mmol) in THF was added. Saturated sodium bicarbonate aqueous solution (500 mL) was added dropwise via addition funnel over 2 hours with vigorous stirring. After 6 hours, a solution of Fmoc-Cl (39 g, 153 mmol) in THF was added slowly. The resulting suspension was stirred for 6 hours at 0° C. The mixture was extracted with ethyl acetate (EA, 500 mL) and the organic layer was retained. The solution was dried with sodium sulfate and evaporated in vacuo. The next step proceeded without purification.

A 1 L, two-necked, round-bottom-flask was fitted with a glass stopper and a calcium tube. A solution of the product from the previous step in MeOH (300 mL) was added and conc. HCl (30 mL, 12 N) was added slowly via addition funnel with magnetic stirring in ice water bath and stirred overnight. The mixture was extracted with EA (1000 mL) and the organic layer was retained. The solution was dried with sodium sulfate and evaporated in vacuo. The residue was purified by recrystallization with n-hexane and EA to give N-Fmoc-N'-methyl hydrazine (32.2 g, 83%). $^1$HNMR (DMSO-D6) δ 7.90~7.88 (d, J=6 Hz, 2H), δ 7.73~7.70 (d, J=9 Hz, 2H), 7.44~7.31 (m, 4H), 4.52~4.50 (d, J=6 Hz, 2H), 4.31~4.26 (t, J=6 Hz, 1H), 2.69 (s, 1H).

(2) Preparation of (N-Fmoc-N'—R$_4$-hydrazino)-acetic acid t-butyl ester

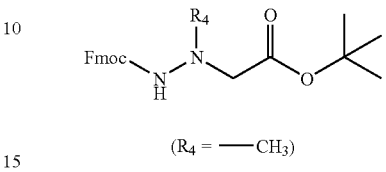

($R_4 = $ —CH$_3$)

A 1 L, two-necked, round-bottom-flask was fitted with a glass stopper and reflux condenser connected to a calcium tube. A solution of N-Fmoc-N'—R$_4$ hydrazine (20 g, 75 mmol) in toluene (300 mL) was added. A solution of t-butyl-bromo acetate (22 g, 111 mmol) in toluene (50 mL) was added slowly. Cs$_2$CO$_3$ (49 g, 149 mmol) was added slowly. NaI (11 g, 74 mmol) was added slowly with vigorous stirring. The reaction mixture was stirred at reflux temperature over 1 day. The product mixture was filtered and extracted with EA (500 mL). The solution was dried over sodium sulfate and evaporated in vacuo. The product was purified by chromatography with hexane:EA=2:1 solution to give (N-Fmoc-N'-methyl-hydrazino)-acetic acid t-butyl ester (19.8 g, 70%). $^1$H-NMR (CDCl$_3$-d) δ 7.78~7.75 (d, J=9 Hz, 2H), δ 7.61~7.59 (d, J=6 Hz, 2H), 7.43~7.26 (m, 4H), 4.42-4.40 (d, J=6 Hz, 2H), 4.23 (b, 1H), 3.57 (s, 2H), 2.78 (s, 3H), 1.50 (s, 9H).

(3) Preparation of (N-Fmoc-N'-methyl-hydrazino)-acetic acid

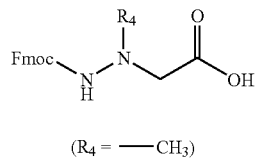

($R_4 = $ —CH$_3$)

A 1 L, two-neck, round-bottomed-flask was fitted with a glass stopper and reflux condenser connected to a calcium tube. (N-Fmoc-N'—R$_4$-hydrazino)-acetic acid t-butyl ester (20 g, 52 mmol) was added. A solution of HCl (150 mL, 4 M solution in dioxane) was added slowly with vigorous stirring in an ice water bath. The reaction mixture was stirred at RT over 1 day. The solution was concentrated completely under reduced pressure at 40° C. A saturated aq. NaHCO$_3$ solution (100 mL) was added and the aqueous layer was washed with diethyl ether (100 mL). Conc. HCl was added dropwise slowly at 0° C. (pH 2-3). The mixture was extracted and the organic layer was retained (500 mL, MC). The solution was dried with sodium sulfate and evaporated in vacuo. The residue was purified by recrystallization with n-hexane and ethyl acetate to give (N-Fmoc-N'-methyl-hydrazino)-acetic acid (12 g, 72%). $^1$H-NMR (DMSO-d$_6$) δ 12.38 (s, 1H), 8.56 (b, 1H), 7.89~7.86 (d, J=9 Hz, 2H), 7.70~7.67 (d, J=9 Hz, 2H), 7.43~7.29 (m, 4H), 4.29~4.27 (d, J=6 Hz, 2H), 4.25~4.20 (t, J=6 Hz, 1H), 3.47 (s, 2H), 2.56 (s, 3H).

Preparation Example 2
Title Compound
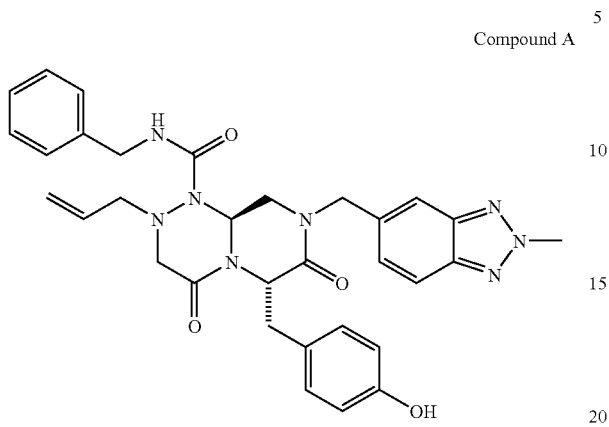
Compound A
To prepare the title compound, the General Scheme of Reverse-Turn Mimetic Library which is described in the above in this specification has been performed by the following scheme:
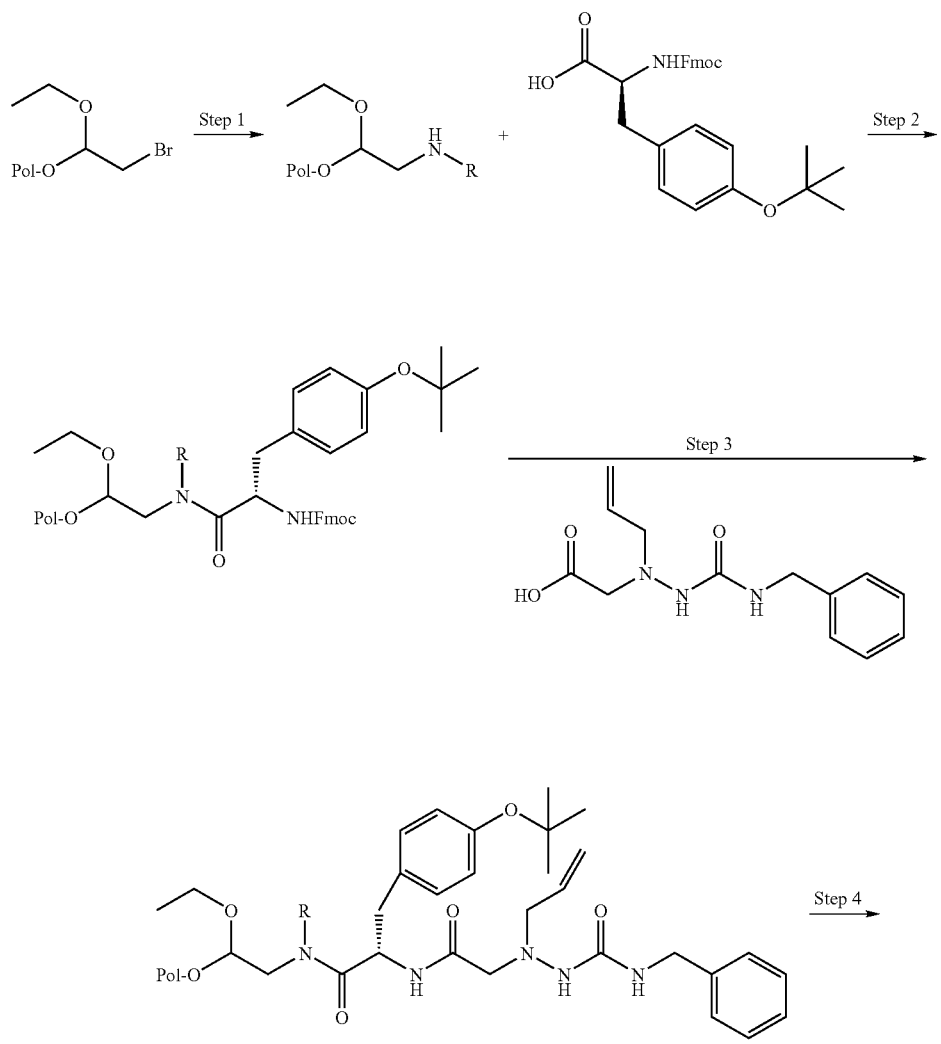

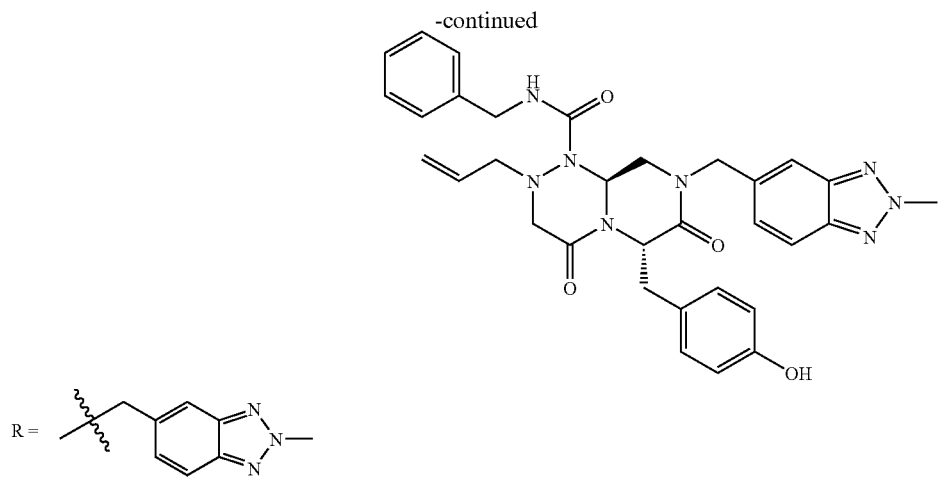

R = 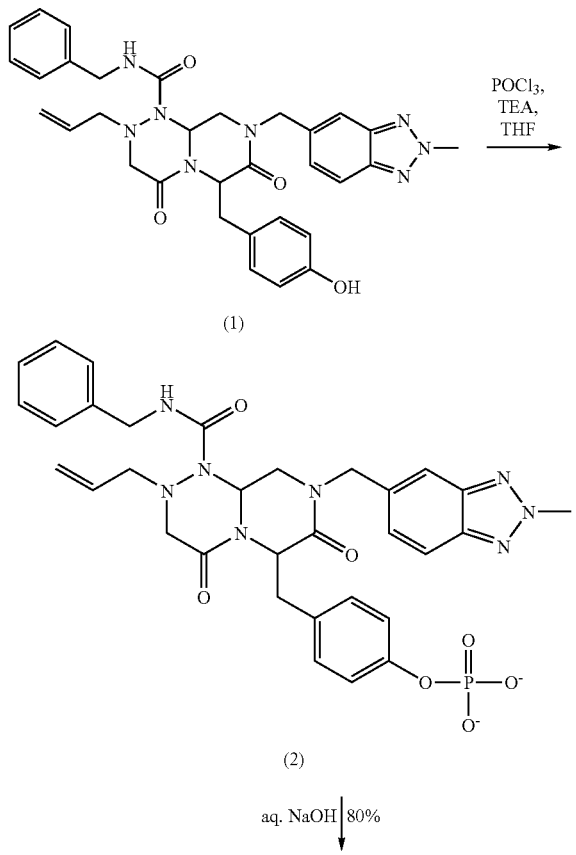

In the above scheme Pe represents a bromoacetal resin (Advanced ChemTech) and detailed procedure is illustrated below:

Step 1

A bromoacetal resin (37 mg, 0.98 mmol/g) and a solution of (2-methyl-2H-benzo[d][1,2,3]triazol-5-yl)methanamine in DMSO (1.4 mL) were placed in a Robbins block (Flex-Chem) having 96 well plates. The reaction mixture was shaken at 60° C. using a rotating oven [Robbins Scientific] for 12 hours. The resin was washed with DMF, MeOH, and then DCM Step 2

A solution of commercial available Fmoc-Tyr(OtBu)-OH (4 equiv.), PyBob (4 equiv.), HOAt (4 equiv.), and DIEA (12 equiv.) in DMF was added to the resin. After the reaction mixture was shaken for 12 hours at room temperature, the resin was washed with DMF, MeOH, and then DCM.

Step 3

To the resin swollen by DMF before reaction was added 25% piperidine in DMF and the reaction mixture was shaken for 30 min at room temperature. This deprotection step was repeated again and the resin was washed with DMF, Methanol, and then DCM. A solution of hydrazine acid (4 equiv.), HOBt (4 equiv.), and DIC (4 equiv.) in DMF was added to the resin and the reaction mixture was shaken for 12 hours at room temperature. The resin was washed with DMF, MeOH, and then DCM.

Step 4

The resin obtained in Step 3 was treated with formic acid (1.2 mL each well) for 18 hours at room temperature. After the resin was removed by filtration, the filtrate was condensed under a reduced pressure using SpeedVac [SAVANT] to give the product as oil. The product was diluted with 50% water/acetonitrile and then lyophilized after freezing. $^1$H NMR (CDCl$_3$): δ 7.849~7.819 (d, J=8.8 Hz, 1H), 7.629 (s, 1H), 7.376~7.209 (m, 5H), 7.003~6.975 (d, J=8.4 Hz, 2H), 6.712~6.670 (t, J=6.0 Hz, 1H), 6.682~6.654 (d, J=8.4 Hz, 2H), 5.698~5.589 (td, J=17.0 Hz, J=10.3 Hz, 1H), 5.438~5.389 (dd, J=10.6 Hz, J=4.0 Hz, 1H), 5.364~5.078 (t, J=5.5 Hz, 1H), 5.112~5.078 (d, J=10.4 Hz, 1H), 4.987~4.927 (d, J=18.0 Hz, 1H), 4.919~4.869 (d, J=14.8 Hz, 1H), 4.682~4.633 (d, J=14.8 Hz, 1H), 4.497 (s, 3H), 4.438~4.270 (qd, J=15.0 Hz, J=6.1 Hz, 2H), 3.479~3.261 (m, 7H).

Preparation Example 3

Preparation of Disodium 4-((2-allyl-1-(benzylcarbamoyl)-8-((2-methyl-2H-benzo[d][1,2,3]triazol-5-yl)methyl)-4,7-dioxo-octahydro-1H-pyrazino[2,1-c][1,2,4]triazin-6-yl)methyl)phenyl phosphate (3)

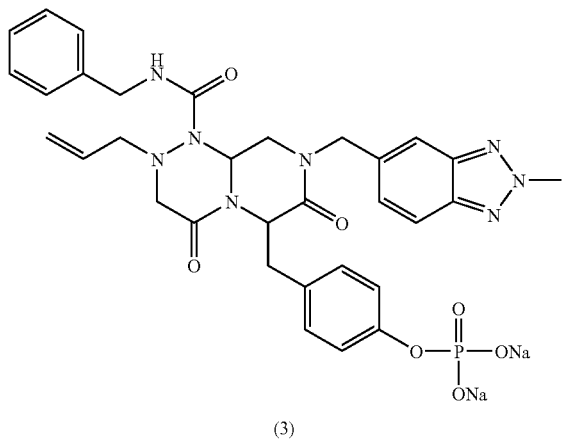

(3)

To a solution of 2-allyl-N-benzyl-6-(4-hydroxybenzyl)-8-((2-methyl-2H-benzo[d][1,2,3]triazol-5-yl)methyl)-4,7-di-oxo-hexahydro-2H-pyrazino[2,1-c][1,2,4]triazine-1(6H)-carboxamide (1) (1.0 eq.) in THF (10 mL/mmol) was added $POCl_3$ (4.0 eq.) and TEA (3.0 eq.) at 0° C. After being stirred at room temperature for 1 hr, sat. aq. $NaHCO_3$ solution was poured slowly and stirred for 1 hr. The resulting mixture was washed with EtOAc, and then the aqueous layer was acidified with 1N aq. HCl solution at 0° C., and then extracted with EtOAc. The organic layer was dried with $Na_2SO_4$ and was concentrated in vacuo. The residue was crystallized with EtOAc and n-Hexane to give an intermediate compound (2) as white solid. The solid was adjusted with 0.1N aq. NaOH solution to pH 11.0 and lyophilized to give the desired compound (3) (80%).

Example 1

P450 CYP3A4 Inhibitory Activity Screening

Test Compounds:

Compound A

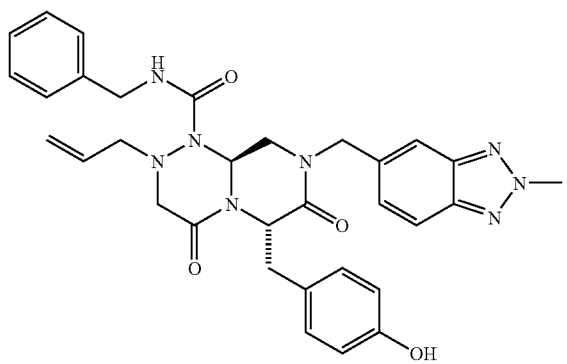

Compound B

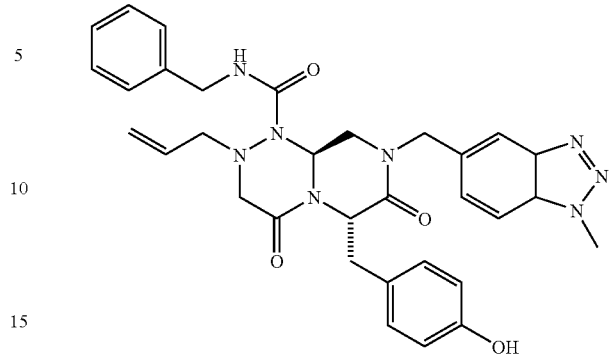

Figure 2:
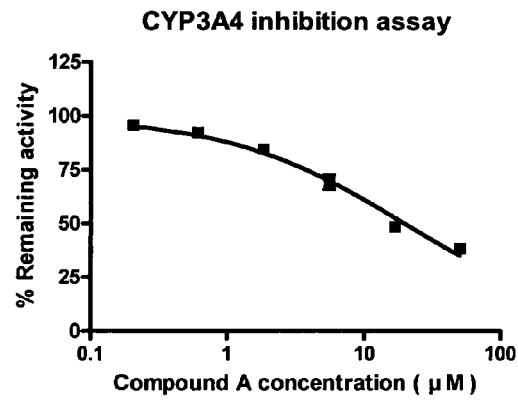
FIG. 2 shows an effect of test compounds (Compounds A and B) on the CYP3A4 activity. The graph is based on the measurement of $IC_{50}$ for Compounds A and B of the present invention of CYP3A4 inhibition assay, wherein inhibition of activity of CYP3A4 was measured at various concentrations of the compound to obtain the $IC_{50}$ value. Detailed procedures are disclosed in Example 1.
Figure 2:
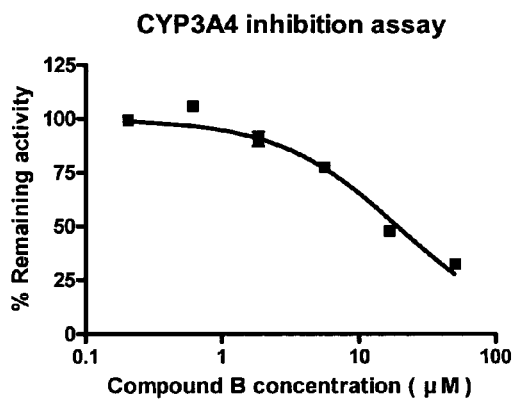

Assay was conducted in a 200 μL volume in 96-well microtiter plates using cDNA-expressed human hepatic CYP3A4 (supersome, BD Gentest™ #456202). 7-Benzyloxy-4-trifluoromethyl-coumarin (BFC) was used as a substrate for CYP3A4. Test articles and substrate BFC were dissolved in 100% acetonitrile. The final volume of acetonitrile in the incubation mixture was less than 1% (volume/volume). Potassium phosphate buffer (pH 7.4, final concentration 0.1 M), $MgCl_2$ (final concentration 8.3 mM), EDTA (final concentration 1.67 mM), a test article stock solution, a CYP3A4 supersome and NADPH (final concentration 0.25 mM) were added to each well. The reaction was initiated by the addition of substrate (BFC, final concentration 30 M) after a 10 min pre-incubation at 37° C. After 10 min incubation at 37° C., the reaction was terminated by the addition of 754 of acetonitrile: 0.5 M Tris-base=4:1 (volume/volume). Thereafter, Fluorescent signal was measured using a fluorometer. BFC metabolite, 7-hydroxy-4-trifluoromethyl-coumarin, was measured using an excitation wavelength of 409 nm and an emission wavelength of 530 nm. FIG. 2 shows IC50 of the test compounds of CYP3A4 inhibition assay. Compounds A and B showed weak inhibition of a CYP3A4 enzyme.

TABLE 6

$IC_{50}$ values of Compound A and Compound B against CYP3A4 activity

| Test compound | $IC_{50}$ (μM) |
|---|---|
| Compound A | 19.2 |
| Compound B | 18.8 |

Example 2

TopFlash reporter gene Bioassay for the measurement of $IC_{50}$ against SW480 cells The test compound (Compound A) used in this example was prepared in Preparation Example 2. SW480 cells were transfected with the usage of Superfect™ transfect reagent (Qiagen, 301307). Cells were trypsinized briefly 1 day before transfection and plated on 6 well plate ($5 \times 10^5$ cells/well) so that they were 50-80% confluent on the day of transfection.

Four microgram (TopFlash) and one microgram (pRL-null) of DNAs were diluted in 150 μl of serum-free medium, and 30 μl of Superfect™ transfect reagent was added. The DNA-Superfect mixture was incubated at room temperature for 15 min, and then, 1 ml of 10% FBS DMEM was added to this complex for an additional 3 hours of incubation. While complexes were forming, cells were washed with PBS twice without antibiotics.

The DNA-Superfect™ transfect reagent complexes were applied to the cells before incubating at 37° C. at 5% $CO_2$ for 3 hours. After incubation, recovery medium with 10% FBS was added to bring the final volume to 1.18 ml. After 3 hours incubation, the cells were harvested and reseeded to a 96 well plate ($3\times10^4$ cells/well). After overnight incubation at 37° C. at 5% $CO_2$, the cells were treated with Compound A for 24 hours. Finally, the activity was checked by means of luciferase assay (Promega, E 1960).

Figure 3:
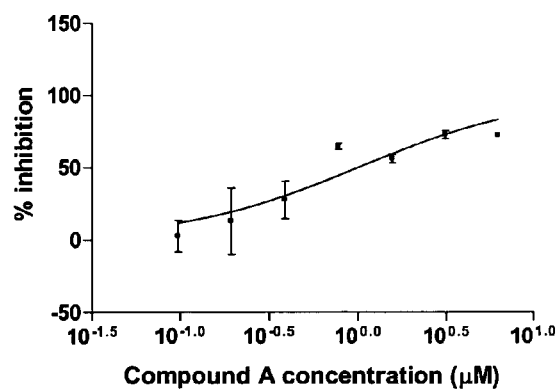
FIG. 3 shows the results of the measurement of $IC_{50}$ of Compound A for SW480 cells on TopFlash Reporter Gene Bioassay.

FIG. 3 illustrates the results of the measurement of $IC_{50}$ of Compound A for SW480 cells. IC50 was 1.003±0.254 μM.

Example 3

Cell Growth Inhibition Activity on AML Cancer Cells

Cell Growth Inhibition Assay

Test Compounds:

Compound A

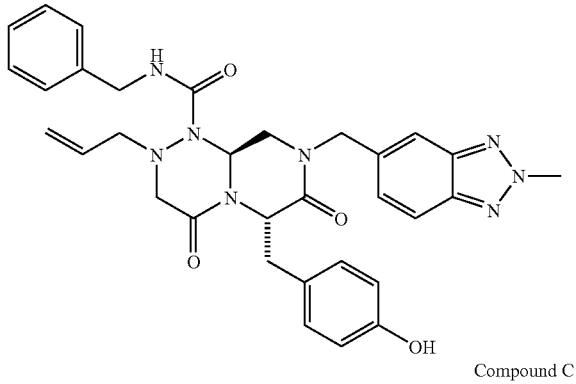

Compound C

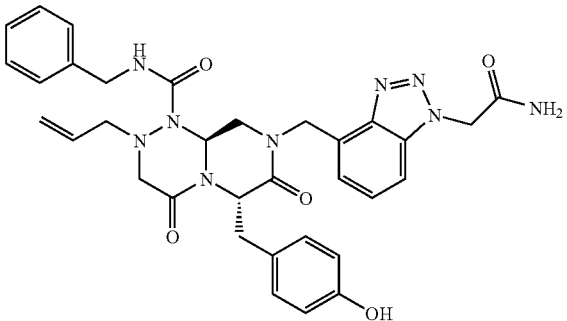

Cell growth Inhibition assay was performed to investigate the rate of inhibition of cell proliferation by the test compounds. MV-4-11 (human, Acute Myeloid Leukemia cell line) cells were cultured in Iscove's modified Dulbecco's medium (IMDM) including 10% fetal bovine serum (FBS), 1× penicillin/streptomycin (10,000 units/ml Penicillin, 10,000 g/ml Streptomycin in 0.85% NaCl). MV-4-11 cells were harvested with IMDM medium and $5\times10^4$ cells/well were transferred to each well of 96 well culture plates (Nunc, #167008). The test compounds were treated with the serial dilution and duplicated for each concentration. For the serial dilution, the test compounds were repeatedly diluted with the same volume of media onto 96-well assay block (costar, #3956). After the dilution, each compound was added to each well. The background absorbance was also measured during the test compounds treatment by adding the IMDM media in replacement of test compound to the negative control plate.

Figure 4:
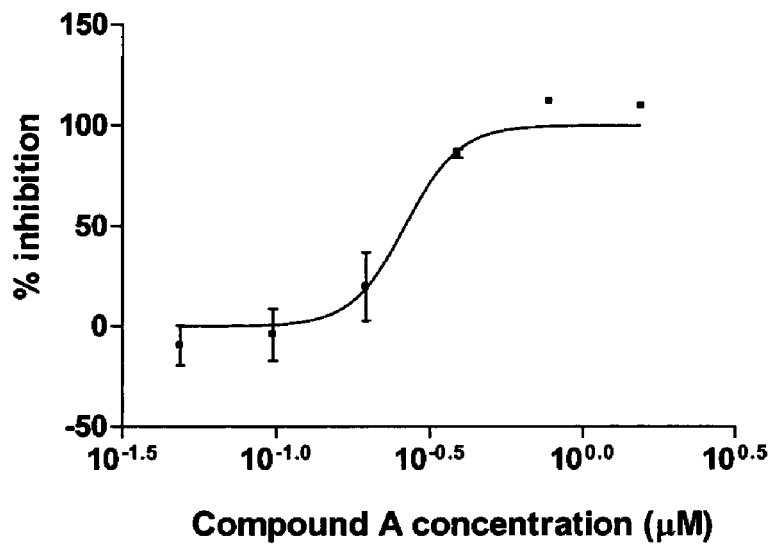
FIG. 4 shows inhibition of growth of AML cancer cells by the test compounds according to the concentration of the test compounds (Compounds A and C).
Figure 4:
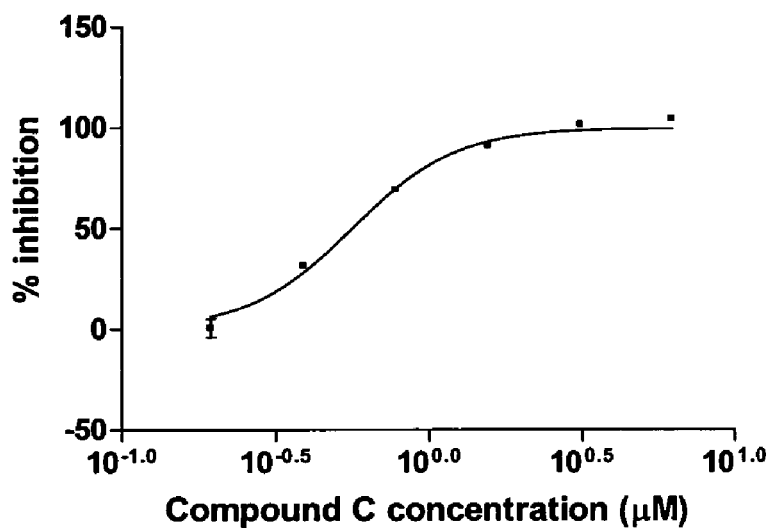

The plates were incubated for 3 days (72 hours) at 37° C. in the humidified incubator containing 5% $CO_2$. On the last day, 20 μL of CellTiter 96 Aqueous One Solution (Promega #G3581) was added to the culture in each well and the plates were incubated for a few hours at 37° C. in the humidified incubator containing 5% $CO_2$. After the incubation, the absorbance of each cell was measured at 490 nm using an EnVision (Perkinelmer, USA). The G150 values were calculated using a Prism 3.0 program. The results showed that the test compounds affected the cell proliferation and inhibited the growth of AML cancer cells. FIG. 4 shows the result of the inhibition of Compound A. GI50 of Compound A and Compound C were 0.262 μM and 0.56 μM.

As described above, the present invention provides new compounds of revers-turn mimetics, which can be used as pharmaceutical compounds, especially on AML cancer cells. The invention has been described in detail with reference to preferred embodiments thereof. However, it will be appreciated by those skilled in the art that changes may be made in these embodiments without departing from the principles and spirit of the invention, the scope of which is defined in the appended claims and their equivalents.

The invention claimed is:

1. A compound having the structure of Formula (III):

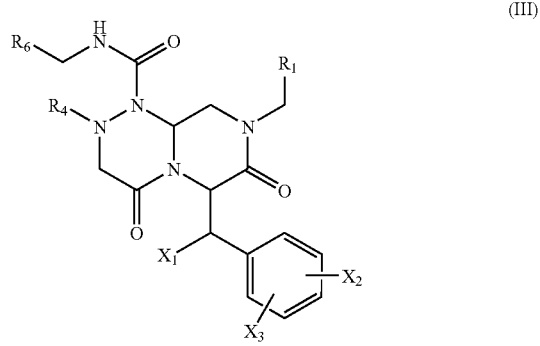

(III)

wherein:
$R_1$ is substituted benzotriazolyl having one or more substituents independently selected from $C_{1-7}$alkyl, carboxyalkyl, $C_{1-2}$alkyl-heterocyclylcarbonylalkyl, and aminocarbonyl;
$R_6$ is phenyl;
$R_4$ is allyl;
$X_1$ is hydrogen; and
each of $X_2$ and $X_3$ is independently hydrogen, hydroxyl, or phosphate.

2. The compound of claim 1 wherein:
$R_1$ is selected from the group consisting of 1-methyl-1H-benzotriazolyl, 2-methyl-2H-benzotriazolyl, 1-ethoxycarbonylmethyl-1H-benzotriazolyl, 1-hydroxycarbonylmethyl-1H-benzotriazolyl, 1-morpholinyl-N-carbonylmethyl-1H-benzotriazolyl, 1-N-methylpiperazinyl-N-carbonylmethyl-1H-benzotriazolyl, 1-aminocarbonylmethyl-1H-benzotriazolyl, 1-methylaminocarbonylmethyl-1H-benzotriazolyl, and 1-pyrdinylmethylaminocarbonylmethyl-1H-benzotriazolyl.

3. The compound of claim 1, wherein $R_1$ is substituted benzotriazolyl having one or more substituents of methyl.

4. A method of treating acute myeloid leukemia, the method comprising: administering to a subject in need thereof a compound of claim 1 in an amount effective to treat acute myeloid leukemia.

* * * * *